US010536057B2

United States Patent
Kawanami et al.

(10) Patent No.: US 10,536,057 B2
(45) Date of Patent: Jan. 14, 2020

(54) MOTOR AND METHOD OF MANUFACTURING MOTOR

(71) Applicant: SONY CORPORATION, Tokyo (JP)

(72) Inventors: Yasunori Kawanami, Tokyo (JP); Kenichiro Nagasaka, Tokyo (JP); Takashi Kito, Kanagawa (JP)

(73) Assignee: SONY CORPORATION, Tokyo (JP)

( * ) Notice: Subject to any disclaimer, the term of this patent is extended or adjusted under 35 U.S.C. 154(b) by 66 days.

(21) Appl. No.: 15/577,591

(22) PCT Filed: Apr. 5, 2017

(86) PCT No.: PCT/JP2017/014294
§ 371 (c)(1),
(2) Date: Nov. 28, 2017

(87) PCT Pub. No.: WO2018/008216
PCT Pub. Date: Jan. 11, 2018

(65) Prior Publication Data
US 2018/0358870 A1    Dec. 13, 2018

(30) Foreign Application Priority Data
Jul. 5, 2016  (JP) .................................. 2016-133558

(51) Int. Cl.
*H02K 11/22*     (2016.01)
*A61B 34/00*     (2016.01)
(Continued)

(52) U.S. Cl.
CPC .......... *H02K 11/22* (2016.01); *A61B 1/00149* (2013.01); *A61B 1/05* (2013.01);
(Continued)

(58) Field of Classification Search
CPC ........ H02K 11/20; H02K 11/21; H02K 11/22; H02K 11/225; H02K 29/08; H02K 29/12
See application file for complete search history.

(56) References Cited

U.S. PATENT DOCUMENTS 5,532,533 A * 7/1996 Mizutani ................ H02K 5/161
310/68 B
6,969,936 B2 * 11/2005 Suzuki ................... H02K 7/003
310/112
(Continued)

FOREIGN PATENT DOCUMENTS

JP    2-290141 A    11/1990
JP    5-23775 U    3/1993
(Continued)

OTHER PUBLICATIONS

International Search Report dated Jul. 4, 2017 in PCT/JP2017/014294, 4 pages (with English translation of Category of Cited Documents).

*Primary Examiner* — Dang D Le
(74) *Attorney, Agent, or Firm* — Xsensus, LLP

(57) ABSTRACT

A motor is provided to reduce a size of a device more effectively. The motor includes a stator, a rotor that is provided to oppose the stator via a clearance, and an encoder that detects a rotation state of the rotor. A hollow space is provided at an inner peripheral side in comparison with the stator and the rotor, and at least a part of the encoder is disposed in the hollow space.

6 Claims, 16 Drawing Sheets

(51) Int. Cl.
*A61B 90/25* (2016.01)
*A61B 1/00* (2006.01)
*A61B 1/05* (2006.01)
*A61H 3/00* (2006.01)
*G01D 5/20* (2006.01)
*G01D 5/347* (2006.01)
*H02K 15/00* (2006.01)
*H02K 21/14* (2006.01)
*B62D 57/02* (2006.01)

(52) U.S. Cl.
CPC .............. *A61B 34/72* (2016.02); *A61B 90/25* (2016.02); *A61H 3/00* (2013.01); *G01D 5/20* (2013.01); *G01D 5/3473* (2013.01); *H02K 15/00* (2013.01); *H02K 21/14* (2013.01); *A61H 2201/1215* (2013.01); *A61H 2201/164* (2013.01); *A61H 2201/165* (2013.01); *A61H 2201/5092* (2013.01); *B62D 57/02* (2013.01)

(56) References Cited

U.S. PATENT DOCUMENTS

| | | | | |
|---|---|---|---|---|
| 7,250,701 B2 * | 7/2007 | Yoshiyama | ............ | H02K 29/08 |
| | | | | 310/166 |
| 8,159,096 B2 * | 4/2012 | Tezuka | ................... | G01D 5/145 |
| | | | | 310/68 B |

FOREIGN PATENT DOCUMENTS

| JP | 10-132611 A | 5/1998 |
|---|---|---|
| JP | 2009-12928 A | 1/2009 |
| JP | 2010-200566 A | 9/2010 |
| JP | 2013-99191 A | 5/2013 |
| JP | 2014-108020 A | 6/2014 |

\* cited by examiner

MOTOR AND METHOD OF MANUFACTURING MOTOR

TECHNICAL FIELD

The present disclosure relates to a motor and a method of manufacturing the motor.

BACKGROUND ART

Nowadays, motors are widely being used as driving sources in every device. Size reduction of a device is desired for various devices. Specifically, for a device using a motor, a technology for achieving size reduction of the motor is proposed for size reduction of the device.

For example, in Patent Literature 1, to provide a technology for reducing a size of an electromechanical device, a technology in which the electromechanical device includes a central axis, a rotor magnet disposed along an outer periphery of the central axis, a rotor having an accommodation space that is open at least in one axial direction of the central axis between the central axis and the rotor magnet, a stator disposed at an outer periphery of the rotor, a revolution number converting mechanism disposed in the accommodation space and integrally configured with the rotor, a load connection unit disposed inside of the stator and configured to connect the revolution number converting mechanism and a rotational load, and a cross-roller bearing provided between the stator and the load connection unit is proposed.

CITATION LIST

Patent Literature

Patent Literature 1: JP 2013-099191A

DISCLOSURE OF INVENTION

Technical Problem

For a device using a motor, it is desirable for size reduction to be performed more effectively. For example, by further reducing a size of the motor used in the device, it is expected that a size of the device will be further reduced. However, it is difficult to further reduce a size of the motor in some cases. Here, generally, an encoder capable of detecting a rotation state of a rotor of a motor is provided in the motor for the purpose of controlling torque output from the motor or the number of revolutions of the motor. Specifically, an axial length of the motor increases in some cases due to the encoder provided in the motor. Therefore, it may be difficult to further reduce a size of the motor.

Accordingly, the present disclosure proposes a novel and improved motor capable of more effectively reducing a size of a device and a method of manufacturing the motor.

Solution to Problem

According to the present disclosure, there is provided a motor including: a stator; a rotor that is provided to oppose the stator via a clearance; and an encoder that is capable of detecting a rotation state of the rotor. A hollow space is provided at an inner peripheral side in comparison with the stator and the rotor, and at least a part of the encoder is disposed in the hollow space.

In addition, according to the present disclosure, there is provided a motor manufacturing method including an alignment process of aligning a rotation axis of a rotor and a central axis of a disc-shaped unit to be detected by using a jig that is capable of being fitted to inner peripheral parts of a rotor extension of a motor and a tubular connecting member. The motor includes a stator, the rotor that is provided at an inner peripheral side in comparison with the stator to oppose the stator via a clearance, a hollow space that is defined by an inner peripheral part of the rotor at the inner peripheral side in comparison with the rotor, an encoder that includes the disc-shaped unit to be detected having an opening at a center thereof and a detecting unit that is capable of detecting a rotation state of the unit to be detected and that includes a disc-shaped substrate having an opening at a center thereof, the encoder being capable of detecting a rotation state of the rotor, a first housing that covers one end and an outer peripheral part of the stator and that is connected to the stator, a second housing that covers the other end of the stator and that is connected to the first housing, a tubular second housing tubular unit that is provided at a center of the second housing and that protrudes toward the hollow space, a second housing extension that extends toward the inner peripheral side from one end of the second housing tubular unit, the rotor extension that is provided at one end side of the rotor and that extends toward the inner peripheral side from an outer peripheral part, the tubular connecting member that connects an inner peripheral part of the unit to be detected and an inner peripheral part of the rotor extension, and a through-hole that penetrates from one end side to the other end side and that is arranged coaxially with a rotation axis of the rotor. At least a part of the encoder is disposed in the hollow space. The substrate is provided opposite the unit to be detected and oppositely connected to one end of the second housing extension. The through-hole penetrates inner peripheral sides of the rotor extension, the connecting member, the unit to be detected, the substrate, and the second housing extension.

Advantageous Effects of Invention

According to the present disclosure, as described above, a size of a device can be more effectively reduced.

Note that the effects described above are not necessarily limitative. With or in the place of the above effects, there may be achieved any one of the effects described in this specification or other effects that may be grasped from this specification.

MODE(S) FOR CARRYING OUT THE INVENTION

Figure 1:
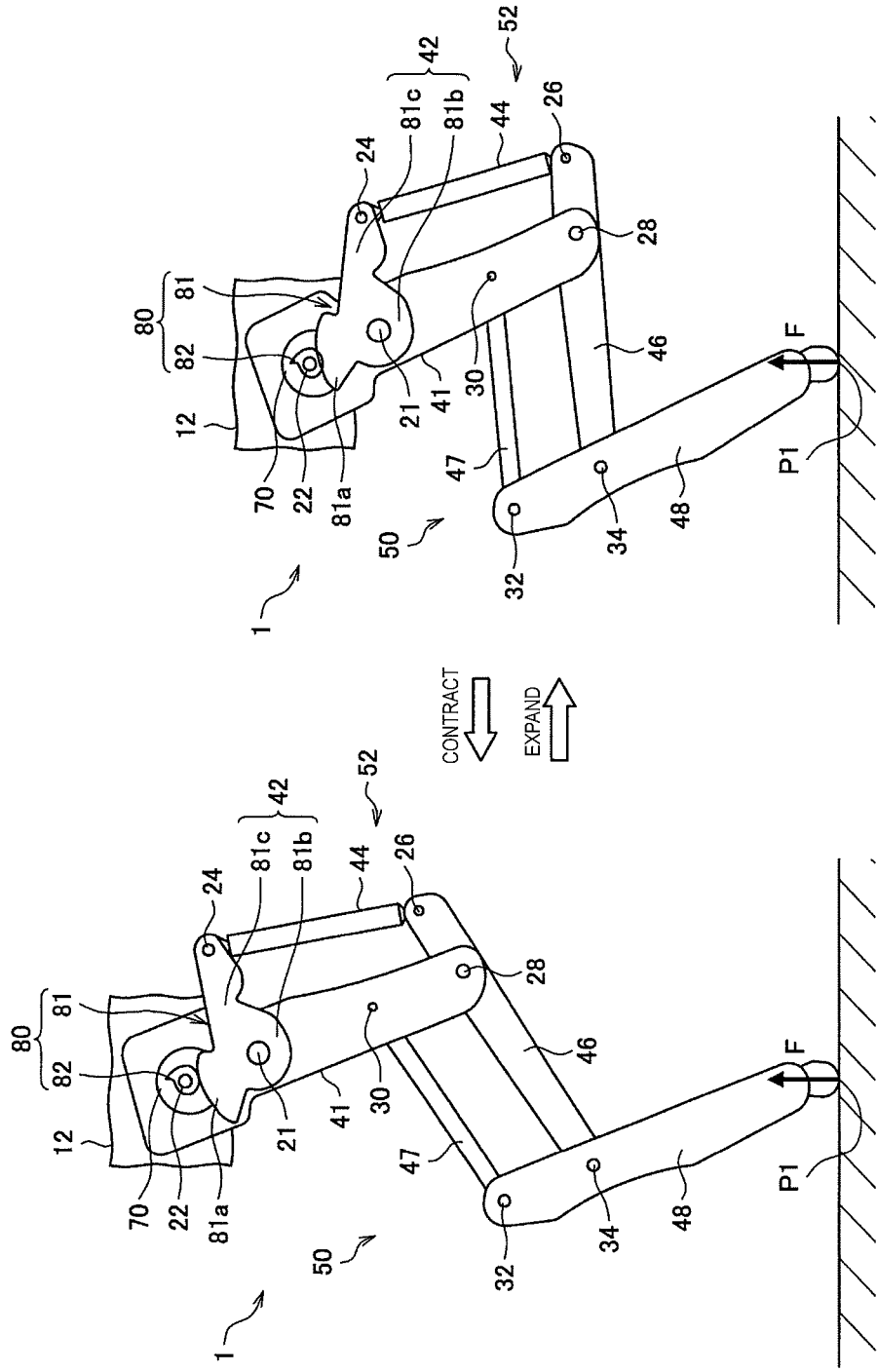
FIG. 1 is a diagram illustrating an example of a schematic configuration of a support device according to an embodiment of the present disclosure.

Hereinafter, (a) preferred embodiment(s) of the present disclosure will be described in detail with reference to the appended drawings. In this specification and the appended drawings, structural elements that have substantially the same function and structure are denoted with the same reference numerals, and repeated explanation of these structural elements is omitted.

The description will be given in the following order.
1. Support device
2. Motor
2-1. Configuration
2-2. Manufacturing method
3. Modified examples
3-1. First modified example
3-2. Second modified example
4. Application examples
4-1. First application example
4-2. Second application example
5. Conclusion

1. SUPPORT DEVICE

First, a support device 1 according to an embodiment of the present disclosure will be described with reference to FIG. 1. FIG. 1 is a diagram illustrating an example of an outline configuration of the support device 1 according to an embodiment of the present disclosure.

For example, the support device 1 according to the present embodiment may be used as a legged robot. Specifically, the support device 1 that supports a robot main body is illustrated in FIG. 1. In FIG. 1, a mounting unit 12, which is a portion of the robot main body at which the support device 1 is mounted, is illustrated in FIG. 1.

The support device 1 includes a link mechanism 50, a motor 70, and a pair of noncircular gears 80. By transmitting power output from the motor 70, the link mechanism 50 is configured to be expandable and contractible according to the power. The support device 1 includes a control device (not illustrated), and for example, driving of the motor 70 may be configured to be controlled on the basis of an operation instruction output from the control device. As will be described below, an encoder capable of detecting a rotation state of a rotor of the motor 70 is provided in the motor 70. A detection result may be output from the encoder to the control device, and the control device may control the driving of the motor 70 on the basis of the detection result. According to the motor 70 according to the present embodiment, a size of the motor 70 can be further reduced by providing the encoder and preventing an increase in dimension of the motor. The motor 70 will be described in detail below.

In the support device 1, the power output from the motor 70 is output to the link mechanism 50 via the pair of noncircular gears 80. The pair of noncircular gears 80 is an example of a pair of rotary bodies as a speed change mechanism that outputs the power output from the motor 70 to the link mechanism 50 at a reduction ratio according to an attitude of the link mechanism 50. The pair of noncircular gears 80 includes an input side gear 82 and an output side gear 81. The input side gear 82 and a rotating shaft of the motor 70 may be directly joined or connected via one or more circular gears. Specifically, in the pair of noncircular gears 80, a change in a reduction ratio according to the attitude of the link mechanism 50 may be realized by a rotational angle of the output side gear 81 having nonlinearity with respect to a rotational angle of the input side gear 82. Hereinafter, the pair of noncircular gears 80 is also simply referred to as noncircular gears 80.

The link mechanism 50 is configured with a plurality of links. Specifically, as illustrated in FIG. 1, the link mechanism 50 includes a link 41, a link 42, which is a part of the output side gear 81, a link 44, a link 46, a link 47, and a link 48.

At least a part of the link mechanism 50 forms a trapezoidal link mechanism 52. For example, in the support device 1, the trapezoidal link mechanism 52 is configured with the link 41, the link 42, the link 44, and the link 46. The trapezoidal link mechanism 52 is a quadric link mechanism in which link lengths of opposing links are made different. The link 42 corresponds to a first link. The link 46 corresponds to a second link. The link 41 and the link 44 correspond to a third link and a fourth link, respectively.

The pair of noncircular gears 80 and the motor 70 are provided at the link 41. The input side gear 82 and the motor 70 are provided at one end side of the link 41. The output side gear 81 is provided further toward a central side than the input side gear 82 in an extending direction of the link 41. The input side gear 82 and the output side gear 81 are connected to the link 41 via respective rotating shafts and are freely rotatable relative to the link 41. For example, the motor 70 is fixed with respect to the link 41. Relative positions of respective rotating shafts of the pair of noncircular gears 80 with respect to the link 41 are fixed. Specifically, relative positions of a rotating shaft 22 of the input side gear 82 and a rotating shaft 21 of the output side gear 81 with respect to the link 41 are fixed.

The one end side of the link 41 is mounted on be relatively rotatable with respect to the mounting unit 12 of the robot main body. Specifically, the link 41 is relatively rotatable around the rotating shaft 22 of the input side gear 82 with respect to the mounting unit 12 of the robot main body. The other end side of the link 41 is connected to a central side of the link 46 and one end side of the link 47 via a shaft unit 28 and a shaft unit 30, respectively, and is relatively rotatable around the shaft unit 28 and the shaft unit 30 with respect to the link 46 and the link 47, respectively. The shaft unit 30 is disposed further toward the central side than the shaft unit 28 in the extending direction of the link 41.

The link 42 corresponds to the input-side first link that is rotatable by power input via the pair of noncircular gears 80. For example, the link 42 is configured with a part of the output side gear 81. Specifically, a tooth unit 81a engaging with a tooth unit of the input side gear 82, a mounting unit 81b connected to the link 41 via the rotating shaft 21, and a protrusion 81c protruding in a radial direction are provided at the output side gear 81. The protrusion 81c is provided at a position different from a position at which the tooth unit 81a is provided in a circumferential direction of the output side gear 81, and a front end side of the protrusion 81c is connected to one end side of the link 44 via a shaft unit 24. The link 42 may be configured with the mounting unit 81b and the protrusion 81c. In this way, the link 42 may be integrally rotatable with the output side gear 81. The link 42 may be relatively rotatable around the shaft unit 24 with respect to the link 44. The link 42 may not be configured with a part of the output side gear 81. The link 42 may be configured with a plurality of members.

The link 46 corresponds to the output-side second link that is disposed opposite the link 42 and is rotatable in accordance with rotation of the link 42. One end side of the link 46 is connected to the other end side of the link 44 via a shaft unit 26 and is relatively rotatable around the shaft unit 26 with respect to the link 44. The other end side of the link 46 is connected to a central side of the link 48 via a shaft unit 34 and is relatively freely rotatable around the shaft unit 34 with respect to the link 48.

As described above, the link 41 and the link 44 respectively correspond to the third link and the fourth link that freely rotatably join the link 42 and the link 46 and are opposite each other.

The other end side of the link 47 is connected to one end side of the link 48 via a shaft unit 32 and is relatively freely rotatable around the shaft unit 32 with respect to the link 48. Other end P1 of the link 48 abuts a floor.

In the support device 1, a parallel link mechanism is configured with the link 41, the link 46, the link 47, and the link 48. Specifically, in the parallel link mechanism, link lengths of the link 41 and the link 48 opposite each other are substantially the same. Specifically, a distance between the shaft unit 30 and the shaft unit 28 and a distance between the shaft unit 32 and the shaft unit 34 are substantially the same. Also, in the parallel link mechanism, link lengths of the link 46 and the link 47 opposite each other are substantially the same. Specifically, a distance between the shaft unit 28 and the shaft unit 34 and a distance between the shaft unit 30 and the shaft unit 32 are substantially the same.

According to the support device 1 illustrated in FIG. 1, by torque output from the motor 70 being transmitted to the link mechanism 50, a floor reaction force F is generated. Specifically, the floor reaction force F having the same magnitude as at least a part of gravity generated due to mass of the robot main body acts on the other end P1 of the link 48. Therefore, at least a part of the mass of the robot main body may be supported. In each of the links, the attitude of the link mechanism 50 is maintained as an attitude in which balance of a given moment is maintained. In the support device 1, a distance between the rotating shaft 22 and the shaft unit 28 in the link 41, a distance between the shaft unit 28 and the shaft unit 34 in the link 46, and a distance between the shaft unit 34 and the other end P1 in the link 48 may have link lengths equal to one another. Also, the link mechanism 50 is configured to be expandable/contractible so that the rotating shaft 22 is disposed above the other end P1 of the link 48 in a vertical direction.

2. MOTOR

Next, the motor 70 according to the present embodiment will be described with reference to FIGS. 2 to 9. Specifically, a method of manufacturing the motor 70 will be described after describing a configuration of the motor 70.

2-1. Configuration

Figure 2:
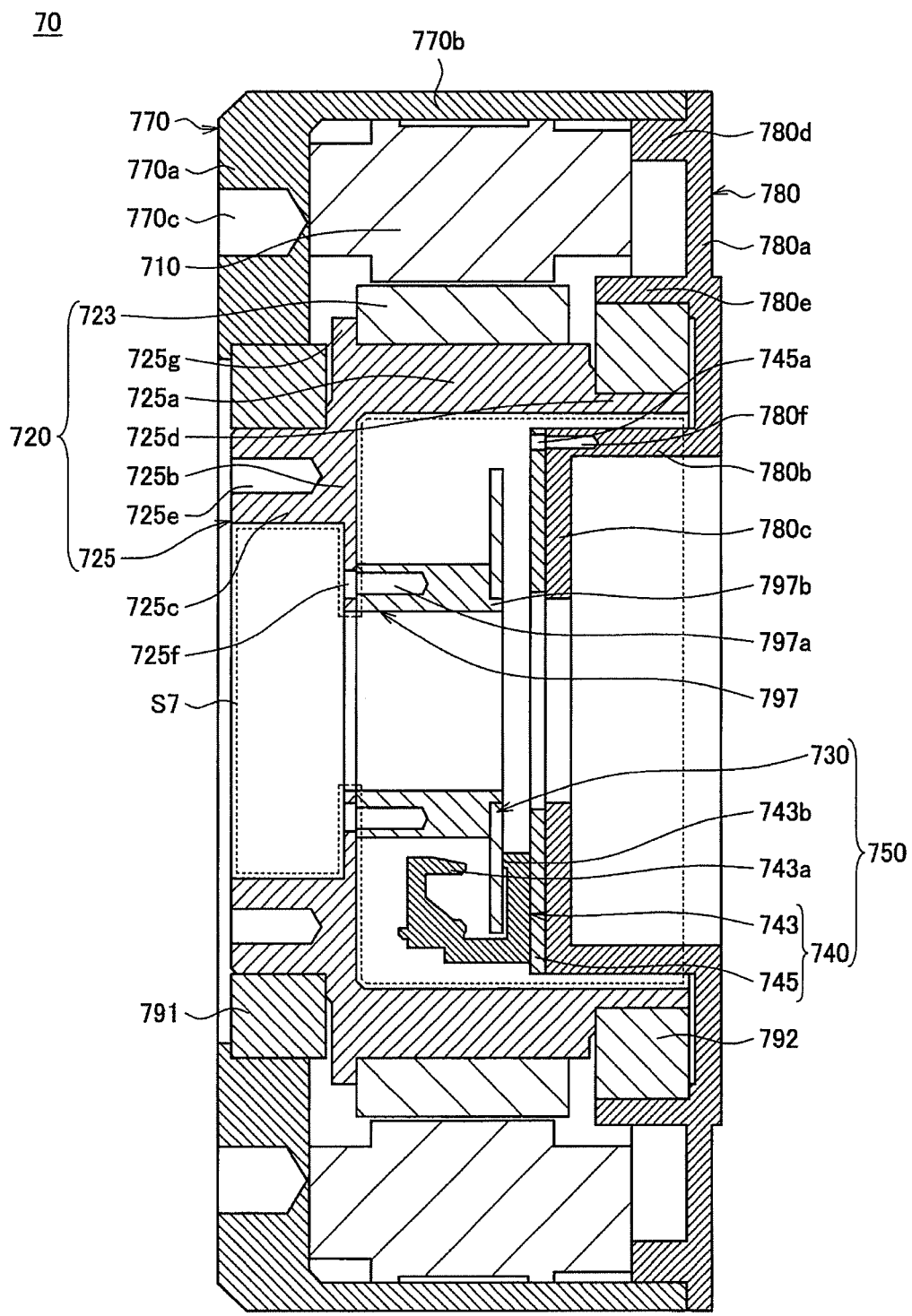
FIG. 2 is a cross-sectional diagram for describing an example of a configuration of a motor according to the present embodiment.

First, the configuration of the motor 70 according to the present embodiment will be described with reference to FIG. 2. FIG. 2 is a cross-sectional diagram for describing an example of the configuration of the motor 70 according to the present embodiment. Specifically, FIG. 2 is a cross-sectional diagram of a cross-section including a rotating shaft of the motor 70. As illustrated in FIG. 2, the motor 70 includes a stator 710, a rotor 720, an encoder 750, a first housing 770, and a second housing 780. Hereinafter, description will be given such that the first housing 770 side with respect to the second housing 780 in an axial direction of the motor 70 is referred to as one end side and the second housing 780 side with respect to the first housing 770 is referred to as the other end side.

The motor 70 may include a through-hole that penetrates from the one end side thereof to the other end side and is arranged coaxially with a rotation axis of the rotor 720. Therefore, a wire connected to another device disposed around the motor 70 may be inserted into the through-hole. Therefore, a wire connecting a device provided at a position closer to one end side than the motor 70 and a device provided on the other end side may be arranged without passing through an outer peripheral side of the motor 70. Accordingly, a size of the support device 1, which is a device in which the motor 70 is used, can be effectively reduced. The through-hole will be described in detail below together with a description of each of the elements.

The stator 710 is provided to oppose the rotor 720 via a clearance. Rotation of the stator 710 relative to a member of the support device 1 to which the motor 70 is mounted is regulated, and the stator 710 may generate a rotating magnetic field for rotating the rotor 720. Specifically, the rotating magnetic field may be generated in the stator 710 by a plurality of armatures disposed in a circumferential direction and power being supplied to the armatures. Also, the stator 710 is tubular. For example, the stator 710 is substantially circularly tubular and extends along the rotation axis of the rotor 720.

For example, the stator 710 includes an iron core having a substantially circularly tubular shape and a plurality of coils. The iron core may be formed by laminating a plurality of steel plates. A plurality of slots are provided in an inner peripheral part of the iron core in a circumferential direction thereof, and a coil is wound around each of the plurality of slots. Specifically, the plurality of slots are equidistantly provided in the circumferential direction of the iron core and extend in an axial direction of the iron core. A plurality of pairs of U-phase, V-phase, and W-phase coils are provided in the stator 710 in the circumferential direction of the iron core. Therefore, the plurality of armatures each corresponding to the U-phase, V-phase, and W-phase are formed by the iron core and the coils. Also, the plurality of pairs of U-phase, V-phase, and W-phase coils in the stator 710 correspond to three-phase windings according to the present disclosure.

For example, each of the coils of the stator 710 is electrically connected to a battery (not illustrated) provided in the support device 1 via a switching circuit including a switching element. Supply of power to each of the coils may be configured to be controlled by the control device controlling the switching element. As described above, the stator 710 has the three-phase windings, and a timing of supply of power to a coil of each of the phases is controlled. A rotating magnetic field rotating in a circumferential direction of the fixer 710 may be generated by controlling the supply of power to each of the coils in this way. In each of the drawings, the shape of the stator 710 is schematically represented by a substantially circular tube to facilitate understanding.

The rotor 720 is provided to oppose the stator 710 via the clearance. A plurality of permanent magnets are provided in the rotor 720, and the rotor 720 is rotatable with respect to the stator 710 by a magnetic force acting on the permanent magnets due to the rotating magnetic field generated by the stator 710. Therefore, for example, the motor 70 may be a brushless DC motor. Specifically, the rotor 720 is tubular and is rotatable around a central axis thereof. The rotation axis of the rotor 720 may be substantially the same as the central axis of the stator 710. As illustrated in FIG. 2, the rotor 720 may be disposed at an inner peripheral side in comparison with the stator 710. In that case, an outer peripheral part of the rotor 720 and an inner peripheral part of the stator 710 oppose each other via the clearance.

For example, the rotor 720 includes a magnet unit 723 and a base 725. The magnet unit 723 is connected to an outer peripheral part of the base 725 and provided in a circumferential direction of the rotor 720. The plurality of permanent magnets are disposed in the magnet unit 723 in the circumferential direction of the rotor 720 such that the plurality of permanent magnets alternately have different polarities. Specifically, the plurality of permanent magnets are disposed so that the polarities on outer peripheral sides of permanent magnets adjacent to each other are different. The plurality of permanent magnets may be equidistantly provided in the circumferential direction of the rotor 720 or may extend in an axial direction of the rotor 720. The magnet unit 723 may include a tubular fixing member to which the plurality of permanent magnets are fixed, and in that case, the fixing member may be connected to the base 725. The fixing member may be configured with various metals. When the fixing member is not included in the magnet unit 723, the plurality of permanent magnets may be directly connected to the base 725. In each of the drawings, a shape of the magnet unit 723 is schematically represented by a circular tube to facilitate understanding.

The base 725 is substantially circularly tubular and may be configured with various metals such as aluminum or various resins such as nylon and polypropylene (PP). A tubular base tubular unit 725*a* that is provided opposite an inner peripheral part of the magnet unit 723 is provided at a central side in an axial direction of the base 725. An outer peripheral part of the base tubular unit 725*a* is connected to the magnet unit 723. For example, the base tubular unit 725*a* is circularly tubular and extends along the rotation axis of the rotor 720. A central axis of the base tubular unit 725*a* may be substantially the same as the rotation axis of the rotor 720.

A base first extension 725*g* extending from one end of the base tubular unit 725*a* toward an outer peripheral side thereof is provided at one end side of the base 725. For example, the base first extension 725*g* is annular. A central axis of the base first extension 725*g* may be substantially the same as the rotation axis of the rotor 720. The other end of the base first extension 725*g* abuts one end of the magnet unit 723. Therefore, a position of the magnet unit 723 in the rotor 720 is prescribed.

A base second extension 725*b* extending from the one end of the base tubular unit 725*a* toward an inner peripheral side is provided at the one end side of the base 725. The base second extension 725*b* corresponds to a rotor extension according to the present disclosure that is provided at one end side of the rotor 720 and extends from an outer peripheral part thereof toward the inner peripheral side. For example, the base second extension 725*b* is disc-shaped and has an opening at a center thereof. A central axis of the base second extension 725*b* may be substantially the same as the rotation axis of the rotor 720. The other end side of an inner peripheral part of the base second extension 725*b* is connected to a connecting member 797.

The connecting member 797 is tubular and may be configured with various metals such as aluminum or various resins such as nylon and PP. The connecting member 797 connects an inner peripheral part of a unit to be detected 730 of the encoder 750, which will be described below, and the inner peripheral part of the base second extension 725*b*. For example, the connecting member 797 is substantially circularly tubular. A central axis of the connecting member 797 may be substantially the same as the rotation axis of the rotor 720. In the connecting member 797, an inner diameter of the connecting member 797 and an inner diameter of the base second extension 725*b* are substantially the same. A connecting member protrusion 797*b* protruding in an axial direction from an inner peripheral side of the other end of the connecting member 797 is provided at the other end side of the connecting member 797. The inner peripheral part of the unit to be detected 730 is connected to the other end of the connecting member 797 in a state in which the inner peripheral part is fitted to an outer peripheral part of the connecting member protrusion 797*b*. A protruding length of the connecting member protrusion 797*b* may be substantially the same as a plate thickness of the unit to be detected 730 of the encoder 750.

For example, mounting of the connecting member 797 to the base second extension 725*b* is realized by screw fastening. For example, a screw mounting hole 797*a* is provided at one end of the connecting member 797. A screw insertion hole 725*f* is provided at a position that is in the inner peripheral part of the base second extension 725*b* and is opposite the screw mounting hole 797*a* of the connecting member 797. The screw insertion hole 725*f* is a so-called clearance hole having an inner diameter larger than an outer diameter of a screw used in the mounting of the connecting member 797 to the base second extension 725*b*. When a countersunk screw is used as the screw, a part of the screw insertion hole 725*f* may have a shape corresponding to a head of the screw. The screw mounting hole 797*a* is a so-called tapped hole in which a female screw unit having a dimension corresponding to a dimension of a male screw unit of the screw is formed.

A base first protrusion 725c protruding in the axial direction from one end of the base second extension 725b is provided at the one end side of the base 725. For example, the base first protrusion 725c is circularly tubular. A central axis of the base first protrusion 725c may be substantially the same as the rotation axis of the rotor 720. Specifically, at one end of the base second extension 725b, the base first protrusion 725c protrudes in the axial direction from the outer peripheral side in comparison with the screw insertion hole 725f. An outer peripheral part of the base first protrusion 725c is press-fitted to an inner peripheral part of a first bearing 791 and thus is freely rotatable integrally with the inner peripheral part of the first bearing 791. Therefore, the base 725 is rotatably supported around the rotation axis by the first bearing 791. A screw mounting hole 725e for mounting an external member of the motor 70 to the base first protrusion 725c may be provided at one end of the base first protrusion 725c.

A base second protrusion 725d protruding in the axial direction from an inner peripheral side of the other end of the base tubular unit 725a is provided at the other end side of the base 725. For example, the base second protrusion 725d is circularly tubular. A central axis of the base second protrusion 725d may be substantially the same as the rotation axis of the rotor 720. An outer peripheral part of the base second protrusion 725d is press-fitted to an inner peripheral part of a second bearing 792 and thus is freely rotatable integrally with the inner peripheral part of the second bearing 792. Therefore, the base 725 is rotatably supported around the rotation axis by the second bearing 792.

According to the present embodiment, a hollow space S7 is defined by the inner peripheral part of the base first protrusion 725c, the inner peripheral part of the base second extension 725b, the inner peripheral part of the base tubular unit 725a, and the inner peripheral part of the base second protrusion 725d of the rotor 720. In this way, according to the present embodiment, the hollow space S7 is defined by an inner peripheral part of the rotor 720. The hollow space S7 is an example of a hollow space according to the present disclosure that is provided at the inner peripheral side in comparison with the stator 710 and the rotor 720.

The first housing 770 and the second housing 780 cover the stator 710. Specifically, the first housing 770 covers one end and an outer peripheral part of the stator 710, and the second housing 780 covers the other end of the stator 710. The first housing 770 is connected to the stator 710, and the second housing 780 is connected to the first housing 770. In the support device 1, for example, the first housing 770 or the second housing 780 is mounted on the external member of the motor 70. Therefore, rotation of the stator 710 relative to the external member is regulated.

The first housing 770 may be configured with various metals such as aluminum or various resins such as nylon and PP. Specifically, the first housing 770 includes a first housing tubular unit 770b provided opposite the outer peripheral part of the stator 710 and a first housing extension 770a provided opposite the one end of the stator 710.

For example, the first housing tubular unit 770b is circularly tubular and extends along the rotation axis of the rotor 720. A central axis of the first housing tubular unit 770b may be substantially the same as the rotation axis of the rotor 720. Specifically, an axial length of the first housing tubular unit 770b is longer than an axial length of the stator 710. Therefore, the outer peripheral part of the stator 710 is covered by the first housing tubular unit 770b. An inner peripheral part of the first housing tubular unit 770b may abut the outer peripheral part of the stator 710.

The first housing extension 770a extends from one end of the first housing tubular unit 770b toward the inner peripheral side. For example, the first housing extension 770a is disc-shaped and has an opening at a center thereof. A central axis of the first housing extension 770a may be substantially the same as the rotation axis of the rotor 720. Specifically, a radial length of the first housing extension 770a is longer than a radial length of the stator 710. Therefore, the one end of the stator 710 is covered by the first housing extension 770a.

The other end of the first housing extension 770a may abut the one end of the stator 710. An outer peripheral part of the first bearing 791 is press-fitted to an inner peripheral part of the first housing extension 770a. Therefore, rotation of the outer peripheral part of the first bearing 791 relative to the stator 710 may be regulated. A screw mounting hole 770c for mounting the external member of the motor 70 to the first housing extension 770a may be provided at one end of the first housing extension 770a.

The second housing 780 may be configured with various metals such as aluminum or various resins such as nylon and PP. Specifically, the second housing 780 includes a disc-shaped annular disc unit 780a that is provided opposite the other end of the stator 710 and has an opening at a center thereof, a tubular second housing first tubular unit 780b protruding from an inner peripheral part of the annular disc unit 780a toward the hollow space S7, and a second housing extension 780c extending from one end of the second housing first tubular unit 780b toward the inner peripheral side. The second housing first tubular unit 780b corresponds to a tubular second housing tubular unit according to the present disclosure that is provided at a center of the second housing 780 and protrudes toward the hollow space S7.

An outer diameter of the annular disc unit 780a is larger than an outer diameter of the stator 710, and an inner diameter of the annular disc unit 780a is smaller than an inner diameter of the stator 710. Therefore, the other end of the stator 710 is covered by the annular disc unit 780a. A central axis of the annular disc unit 780a may be substantially the same as the rotation axis of the rotor 720.

A tubular second housing second tubular unit 780d protruding toward one end side is provided at an outer peripheral side of the annular disc unit 780a. For example, the second housing second tubular unit 780d is circularly tubular. A central axis of the second housing second tubular unit 780d may be substantially the same as the rotation axis of the rotor 720. An outer peripheral part of the second housing second tubular unit 780d is fitted to an inner peripheral side of the other end of the first housing tubular unit 770b. An outer peripheral part of the annular disc unit 780a protrudes by a thickness of the first housing tubular unit 770b toward the outer peripheral side in comparison with the second housing second tubular unit 780d. In the outer peripheral part of the annular disc unit 780a, one end side of a portion protruding in this way abuts the other end of the first housing tubular unit 770b. Therefore, an axial position of the second housing 780 with respect to the first housing 770 is prescribed. For example, the second housing second tubular unit 780d is fixed to the other end of the first housing tubular unit 770b by screw fastening. Therefore, the second housing 780 is fixed to the first housing 770. One end of the second housing second tubular unit 780d may abut the other end of the stator 710.

A tubular second housing third tubular unit 780e protruding toward one end side is provided at the inner peripheral side in comparison with the second housing second tubular unit 780d in the annular disc unit 780a. For example, the second housing third tubular unit 780e is circularly tubular. A central axis of the second housing third tubular unit 780e may be substantially the same as rotation axis of the rotor 720. An outer peripheral part of the second bearing 792 is press-fitted to an inner peripheral part of the second housing third tubular unit 780e. Therefore, rotation of the outer peripheral part of the second bearing 792 relative to the stator 710 may be regulated.

For example, the second housing first tubular unit 780b is circularly tubular. A central axis of the second housing first tubular unit 780b may be substantially the same as rotation axis of the rotor 720. An outer diameter of the second housing first tubular unit 780b is smaller than inner diameters of the base tubular unit 725a and the base second protrusion 725d Therefore, the second housing first tubular unit 780b may protrude from the inner peripheral part of the annular disc unit 780a toward the hollow space S7 without interfering with the base 725.

For example, the second housing extension 780c is disc-shaped and has an opening at a center thereof. A central axis of the second housing extension 780c may be substantially the same as rotation axis of the rotor 720. A substrate 745 of the encoder, which will be described below, is oppositely connected to one end of the second housing extension 780c. For example, mounting of the substrate 745 to the second housing extension 780c is realized by screw fastening. For example, a screw mounting hole 780f is provided at an outer peripheral part of the second housing extension 780c. A screw insertion hole 745a is provided at a position that is in an outer peripheral part of the substrate 745 and is opposite the screw mounting hole 780f of the second housing extension 780c. The screw insertion hole 745a is a so-called clearance hole having an inner diameter larger than an outer diameter of a screw used in the mounting of the substrate 745 to the second housing extension 780c. When a countersunk screw is used as the screw, a part of the screw insertion hole 745a may have a shape corresponding to a head of the screw. The screw mounting hole 780f is a so-called tapped hole in which a female screw unit having a dimension corresponding to a dimension of a male screw unit of the screw is formed.

The encoder 750 is able to detect a rotation state of the rotor 720. The encoder 750 outputs a detection result to the control device of the support device 1. As described above, the detection result output from the encoder 750 is used by the control device to control the driving of the motor 70. Specifically, the encoder 750 may detect a rotational angle corresponding to a rotational position of the rotor 720 at each time and output information indicating a record of the rotational angle of the rotor 720 as the detection result. The encoder 750 may calculate a number of revolutions of the rotor 720 on the basis of the detected record of the rotational angle of the rotor 720 and output information indicating the number of revolutions as the detection result.

For example, the encoder 750 includes the unit to be detected 730 and a detecting unit 740 configured to detect a rotation state of the unit to be detected 730. The type of the encoder 750 of the motor 70 is not particularly limited, and various encoders may be applied as the encoder 750. Hereinafter, an example in which the encoder 750 is an optical encoder using transmission of light will be described.

As described above, the unit to be detected 730 is connected to the base second extension 725b of the base 725 of the rotor 720 via the connecting member 797. Therefore, the unit to be detected 730 may be integrally rotatable with the rotor 720. Specifically, the unit to be detected 730 is disc-shaped and has an opening at a center thereof. A central axis of the unit to be detected 730 may be substantially the same as rotation axis of the rotor 720. An outer diameter of the unit to be detected 730 is smaller than the inner diameters of the base tubular unit 725a and the base second protrusion 725d. Therefore, the unit to be detected 730 may be disposed in the hollow space S7 without interfering with the base 725.

In the unit to be detected 730, a light transmitting unit 730a (see FIG. 5) configured to transmit radiated light and a light shielding unit 730b (see FIG. 5) configured to shield the radiated light are alternately provided in the circumferential direction of the rotor 720. In the unit to be detected 730, a portion in which the light transmitting unit 730a and the light shielding unit 730b are provided is disposed between a radiating unit 743a and a light receiving unit 743b of a sensor 743 of the detecting unit 740. Specifically, in the unit to be detected 730, the radiating unit 743a of the sensor 743 of the detecting unit 740 is disposed at one end side of the portion in which the light transmitting unit 730a and the light shielding unit 730b are provided, and the light receiving unit 743b of the sensor 743 of the detecting unit 740 is disposed at the other end side. As will be described below, one end side of the unit to be detected 730 is configured to be irradiated with light from the radiating unit 743a.

For example, the detecting unit 740 includes the sensor 743 and the disc-shaped substrate 745 having an opening at a center thereof. Specifically, in the detecting unit 740, the sensor 743 is connected to a part of one end side of the outer peripheral part of the substrate 745.

The radiating unit 743a configured to irradiate the unit to be detected 730 with light and the light receiving unit 743b configured to receive light transmitted through the light transmitting unit 730a are provided in the sensor 743. Specifically, a function of the radiating unit 743a radiating light may be realized by a light emitting diode (LED). The light receiving unit 743b may output a signal indicating a light reception result to the substrate 745, and for example, by the signal being processed in the substrate 745, a detection result related to the rotation state of the unit to be detected 730 may be generated. For example, the substrate 745 is connected to the control device of the support device 1 via a wire. Therefore, the detection result related to the rotation state of the unit to be detected 730 is output from the substrate 745 to the control device as a detection result related to the rotation state of the rotor 720. In this way, the detecting unit 740 may detect the rotation state of the unit to be detected 730 on the basis of the light reception result from the light receiving unit 743b.

Specifically, the radiating unit 743a and the light receiving unit 743b are oppositely disposed, and as described above, the portion in which the light transmitting unit 730a and the light shielding unit 730b are provided in the unit to be detected 730 is disposed between the radiating unit 743a and the light receiving unit 743b. For example, in a case in which the rotor 720 rotates in one direction, by the unit to be detected 730 integrally rotating in the one direction with the rotor 720, a state in which light radiated from the radiating unit 743a transmits through the light transmitting unit 730a and a state in which the light is shielded by the light shielding unit 730b are alternately repeated. Because a value of a signal indicating the light reception result acquired by the light receiving unit 743b may correspond to intensity of received light, a signal indicating a light reception result acquired by the light receiving unit 743b is a pulse waveform signal in the case in which the unit to be detected 730 rotates in one direction. For example, on the basis of the number of pulses in the signal indicating the light reception result, the detecting unit 740 may generate a rotational position of the unit to be detected 730 as a detection result related to the rotation state of the unit to be detected 730. Therefore, detection of the rotation state of the rotor 720 by the encoder 750 is realized.

As described above, the substrate 745 is connected to the second housing extension 780c of the second housing 780. Therefore, rotation of the detecting unit 740 relative to the stator 710 may be regulated. A central axis of the substrate 745 may be substantially the same as rotation axis of the rotor 720. An outer diameter of the substrate 745 is smaller than the inner diameters of the base tubular unit 725a and the base second protrusion 725d. Therefore, the unit to be detected 730 may be disposed in the hollow space S7 without interfering with the base 725. The substrate 745 is provided opposite the unit to be detected 730.

A wire for outputting a detection result from the encoder 750 to the control device of the support device 1 is connected to the substrate 745 in some cases. Here, in the present embodiment, as described above, the unit to be detected 730 is provided to be integrally rotatable with the rotor 720, and the rotation of the detecting unit 740 relative to the stator 710 is regulated. Therefore, the wire connected to the detecting unit 740 can be prevented from rotating together with rotation of the rotor 720. Therefore, because a space for disposing the wire may be saved, a size of the support device 1, which is a device in which the motor 70 is used, can be effectively reduced.

The unit to be detected 730 is connected to the other end side of the inner peripheral part of the base second extension 725b, which is provided at the one end side of the rotor 720 and extends from the outer peripheral part toward the inner peripheral side, via the connecting member 797 as described above. The substrate 745 of the detecting unit 740 is connected to the one end of the second housing extension 780c that extends toward the inner peripheral side from the one end of the second housing first tubular unit 780b, which is provided at the center of the second housing 780 and protrudes toward the hollow space S7 as described above. Therefore, the unit to be detected 730 and the detecting unit 740 of the encoder 750 are disposed in the hollow space S7 defined by the inner peripheral part of the rotor 720. Specifically, the encoder 750 is disposed in a space at inner peripheral sides of the base tubular unit 725a and the base second protrusion 725d of the base 725 of the rotor 720. For example, the inner diameters of the base tubular unit 725a and the base second protrusion 725d may be set to 40 mm or larger.

In this way, according to the present embodiment, at least a part of the encoder 750 is disposed in the hollow space provided at the inner peripheral side in comparison with the stator 710 and the rotor 720. Therefore, a portion provided at the inner peripheral side in comparison with the stator 710 and the rotor 720 can be effectively used as a portion in which the encoder 750 is provided. Accordingly, by providing the encoder 750 in the motor 70, an increase in dimension of the motor 70 can be prevented. Specifically, by providing the encoder 750 in the motor 70, an increase in axial length of the motor 70 can be prevented. Consequently, a size of the motor 70 can be further reduced. Accordingly, a size of the support device 1 can be effectively reduced. Furthermore, weights of the motor 70 and the support device 1 using the motor 70 may be reduced.

Further, the through-hole that penetrates from one end side to the other end side and is arranged coaxially with the rotation axis of the rotor 720 penetrates through inner peripheral sides of the unit to be detected 730 and the substrate 745. Specifically, by the central axes of the unit to be detected 730 and the substrate 745 that are provided opposite each other are substantially the sameing the rotation axis of the rotor, the through-hole may penetrate through the inner peripheral sides of the unit to be detected 730 and the substrate 745. In this way, by the through-hole penetrating through the inner peripheral sides of the unit to be detected 730 and the substrate 745, the through-hole may be made to penetrate from one end side to the other end side and be arranged coaxially with the rotation axis of the rotor 720 while the encoder 750 is disposed in the hollow space S7.

The through-hole that penetrates from one end side to the other end side and is arranged coaxially with the rotation axis of the rotor 720 penetrates through inner peripheral sides of the base second extension 725b, the connecting member 797, and the second housing extension 780c. Specifically, by the central axes of the base second extension 725b, the connecting member 797, and the second housing extension 780c are substantially the sameing the rotation axis of the rotor, the through-hole may penetrate through the inner peripheral sides of the base second extension 725b, the connecting member 797, and the second housing extension 780c. Therefore, in the motor 70, making the through-hole penetrate from one end side to the other end side and be arranged coaxially with the rotation axis of the rotor 720 may be realized.

The encoder 750 may detect a phase of a current flowing in the three-phase windings of the stator 710. For example, on the basis of the detection result related to the rotation state of the rotor 720, the encoder 750 may detect a phase of a current flowing in the three-phase windings of the stator 710 by calculating an electrical angle in the stator 710.

2-2. Manufacturing Method

Next, a method of manufacturing the motor 70 according to the present embodiment will be described with reference to FIGS. 3 to 9. The method of manufacturing the motor 70 includes a component processing process for processing each component constituting the motor 70 and an assembling process for assembling each of the components.

In the component processing process, each of the components constituting the motor 70 is formed by using a variety of processing. For example, the first housing 770, the second housing 780, the connecting member 797, and the base 725 of the rotor 720 may be formed by properly using cutting processing, injection molding, casting, press processing, or the like. The stator 710, the magnet unit 723 of the rotor 720, and the encoder 750 may be formed through, in addition to a process of performing processing of members constituting each of the stator 710, the magnet unit 723 of the rotor 720, and the encoder 750, a process of connecting each of the members.

In the assembling process, the motor 70 is assembled such that a positional relation of each of the components is a desired positional relation. The assembling process includes a first assembling process, a second assembling process, and a third assembling process. In the assembling process, assembling using a jig is performed. Specifically, in the assembling process, in a state in which the jig is installed, an assembly including each of the components is assembled. In the assembling process, a pre-assembling process in which some of the components constituting the motor 70 are pre-assembled before the first assembling process, the second assembling process, and the third assembling process, which will be described below, is included.

In the pre-assembling process, the detecting unit 740 of the encoder 750 is mounted on the second housing 780. Specifically, by a screw being inserted into the screw insertion hole 745a of the substrate 745 of the detecting unit 740 and being screwed to the screw mounting hole 780f of the second housing 780, the detecting unit 740 is mounted on the second housing extension 780c of the second housing 780. The second bearing 792 is press-fitted to the inner peripheral part of the second housing third tubular unit 780e of the second housing 780.

In the pre-assembling process, the connecting member 797 and the unit to be detected 730 of the encoder 750 are connected. The magnet unit 723 of the rotor 720, the base 725 of the rotor 720, and the first bearing 791 are connected. The first housing 770 and the stator 710 are connected. Various connection methods such as adhering by an adhesive, joining by welding, and fastening by a screw may be applied to the connection between each of the components in the pre-assembling process.

According to the present embodiment, in the assembling process, dimension precision in the motor 70 can be improved by using the jig. Hereinafter, the assembling process will be described in detail.

(Jig)

Figure 3:
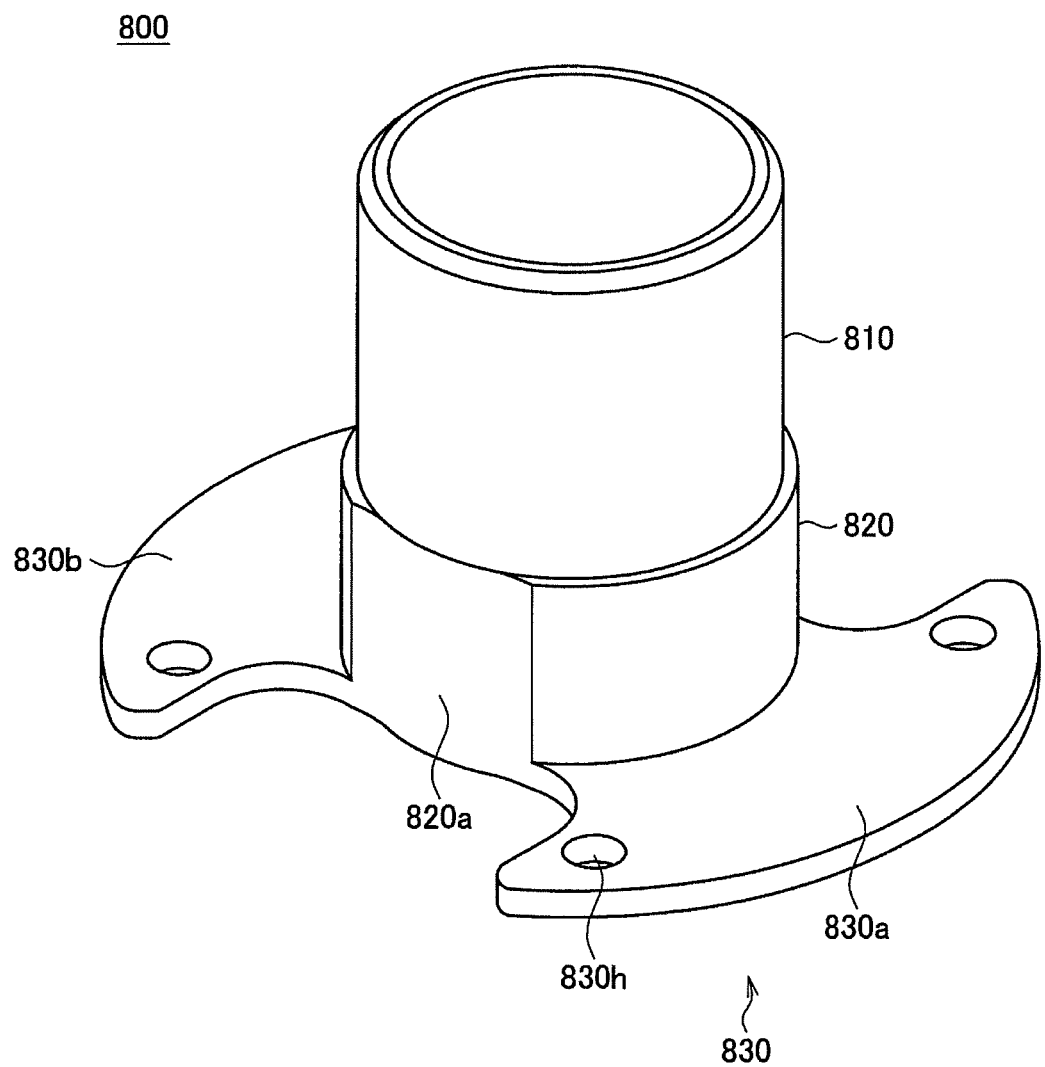
FIG. 3 is a perspective diagram for describing an example of a configuration of a jig used in a method of manufacturing the motor according to the present embodiment.

First, before describing the first assembling process, the second assembling process, and the third assembling process, a jig 800 used in the assembling process will be described with reference to FIG. 3. FIG. 3 is a perspective diagram for describing an example of a configuration of the jig 800 used in the method of manufacturing the motor 70 according to the present embodiment.

The jig 800 may be configured with various metals such as aluminum or various resins such as nylon and PP. As illustrated in FIG. 3, the jig 800 includes a small diameter part 810, a large diameter part 820, and a mounting unit 830.

The small diameter part 810 can be fitted to inner peripheral parts of the base second extension 725b of the base 725 and the connecting member 797. Therefore, the small diameter part 810 has a shape corresponding to the inner peripheral parts of the base second extension 725b and the connecting member 797. For example, the small diameter part 810 is tubular. Specifically, the small diameter part 810 is circularly tubular. An outer diameter of the small diameter part 810 is smaller than the inner diameters of the base second extension 725b and the connecting member 797. Specifically, the outer diameter of the small diameter part 810 may be set to a value in which the small diameter part 810 can be fitted by a clearance fit to the inner peripheral parts of the base second extension 725b and the connecting member 797. A front end side of the small diameter part 810 has an opening, and a rear end side thereof is connected to the large diameter part 820.

The large diameter part 820 can be fitted to an inner peripheral part of the second housing extension 780c of the second housing 780. Therefore, the large diameter part 820 has a shape corresponding to the inner peripheral part of the second housing extension 780c. For example, the large diameter part 820 is substantially tubular. Specifically, the large diameter part 820 is substantially circularly tubular. An outer diameter of the large diameter part 820 is smaller than an inner diameter of the second housing extension 780c. Specifically, the outer diameter of the large diameter part 820 may be set to a value in which the large diameter part 820 can be fitted by a clearance fit to the inner peripheral part of the second housing extension 780c. A central axis of the large diameter part 820 may be substantially the same as central axis of the small diameter part 810. An inner diameter of the large diameter part 820 may be substantially the same as inner diameter of the small diameter part 810. In other words, a cylindrical space may be defined by an inner peripheral part of the large diameter part 820 and an inner peripheral part of the small diameter part 810. A rear end side of the large diameter part 820 is connected to the mounting unit 830. As illustrated in FIG. 3, the large diameter part 820 may have a region 820a, whose outer diameter is small in comparison to other portions, at a portion in the circumferential direction.

The mounting unit 830 extends from a rear end of the large diameter part 820 toward the outer peripheral side. Specifically, the mounting unit 830 includes a first mounting unit 830a extending from one side of the rear end of the large diameter part 820 toward the outer peripheral side and a second mounting unit 830b extending from the other side of the rear end of the large diameter part 820 toward the outer peripheral side. For example, the first mounting unit 830a and the second mounting unit 830b are plate-shaped. Front ends of the first mounting unit 830a and the second mounting unit 830b have an arc shape arranged coaxially with the large diameter part 820 and protrude toward both sides in the circumferential direction.

A screw insertion hole 830h is provided in each of the first mounting unit 830a and the second mounting unit 830b. Specifically, in the front ends of the first mounting unit 830a and the second mounting unit 830b, the screw insertion hole 830h is provided at each of the portions protruding toward both of the sides in the circumferential direction. The screw insertion hole 830h is a so-called clearance hole that is provided for mounting the jig 800 to the second housing 780 and has an inner diameter larger than an outer diameter of a screw used in the mounting of the jig 800 to the second housing 780. When a countersunk screw is used as the screw, a part of the screw insertion hole 830h may have a shape corresponding to a head of the screw.

Although an example in which the small diameter part 810 and the large diameter part 820 are hollows is illustrated in FIG. 3, the small diameter part 810 and the large diameter part 820 may be solids.

(First Assembling Process)

Figure 4:
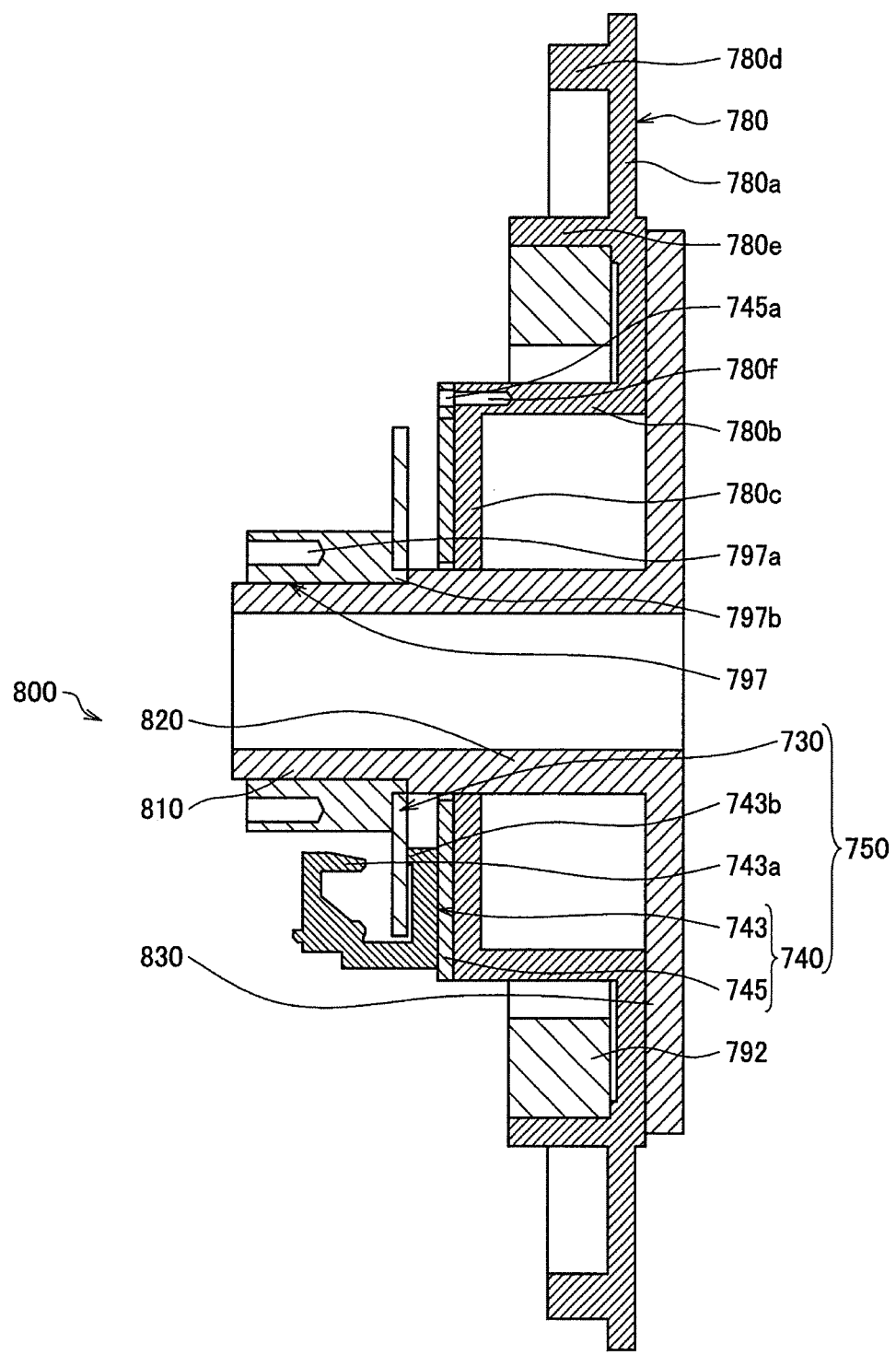
FIG. 4 is a cross-sectional diagram illustrating an example of an assembly including a connecting member, an encoder, and a second housing assembled in a first assembling process.
Figure 5:
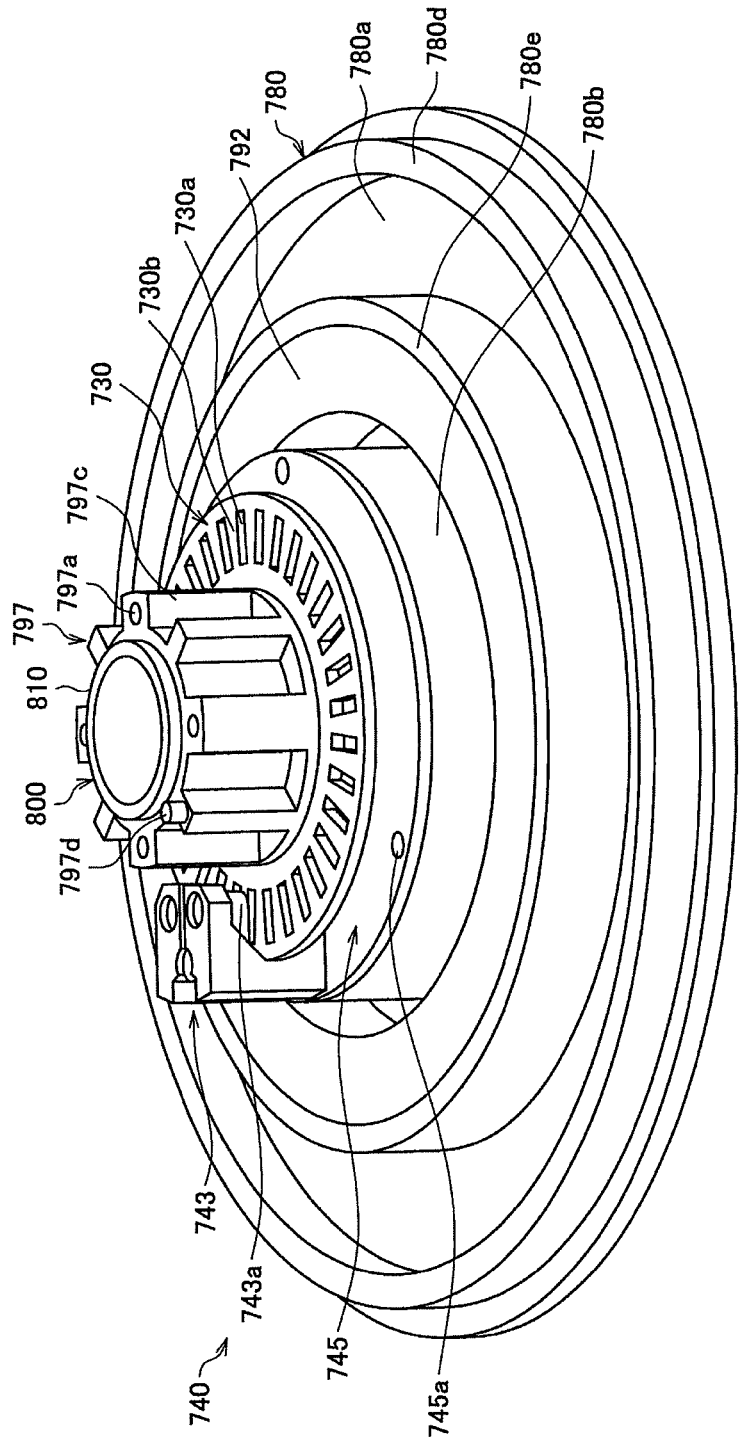
FIG. 5 is a perspective diagram illustrating the example of the assembly including the connecting member, the encoder, and the second housing assembled in the first assembling process.

Next, the first assembling process will be described with reference to FIGS. 4 and 5. FIG. 4 is a cross-sectional diagram illustrating an example of an assembly including the connecting member 797, the encoder 750, and the second housing 780 assembled in the first assembling process. FIG. 5 is a perspective diagram illustrating the example of the assembly including the connecting member 797, the encoder 750, and the second housing 780 assembled in the first assembling process.

In the first assembling process, first, the connecting member 797, the unit to be detected 730 of the encoder 750, the detecting unit 740 of the encoder 750, and the second housing 780 are mounted on the jig 800. Specifically, as illustrated in FIG. 4, the mounting of each of the members to the jig 800 is performed so that one end of the mounting unit 830 of the jig 800 and the other end of the annular disc unit 780a of the second housing 780 are opposite each other, and one end of the substrate 745 of the detecting unit 740 and the other end of the unit to be detected 730 are opposite each other. As illustrated in FIG. 4, the mounting of each of the members to the jig 800 is performed so that the inner peripheral part of the second housing extension 780c of the second housing 780 is fitted to the outer peripheral part of the large diameter part 820 of the jig 800, and the inner peripheral part of the connecting member 797 is fitted to an outer peripheral part of the small diameter part 810 of the jig 800.

In this way, the jig 800 can be fitted to the inner peripheral parts of the connecting member 797 and the second housing extension 780c. Therefore, dimension precision in alignment of the central axes of the connecting member 797, the unit to be detected 730, and the second housing 780 may be more easily improved.

In FIG. 5, an exterior of the assembly including the connecting member 797, the encoder 750, and the second housing 780 assembled in the first assembling process and the jig 800 are illustrated. As illustrated in FIG. 5, a plurality of groove units 797c may be provided at intervals in the circumferential direction at the outer peripheral part of the connecting member 797, and the groove units 797c may extend in the axial direction. A plurality of screw mounting holes 797a may be provided at intervals in the circumferential direction at the one end of the connecting member 797. A protrusion 797d for determining a position of the base 725 with respect to the connecting member 797 when mounting the base 725 to the connecting member 797 may be provided at the one end of the connecting member 797. A plurality of screw insertion holes 745a may be provided at intervals in the circumferential direction at the outer peripheral part of the substrate 745.

In the second housing 780, a screw mounting hole may be provided at a position corresponding to the screw insertion hole 830h of the mounting unit 830 of the jig 800 illustrated in FIG. 3, and in that case, the mounting unit 830 of the jig 800 may be mounted on the second housing 780 using a screw. In the assembling process, assembling of the motor 70 is performed mostly in a state in which the other end of the mounting unit 830 of the jig 800 is grounded to the floor. In other words, in the assembling process, the other end side of the motor 70 mostly faces downward vertically. Therefore, in the assembling process, as illustrated in FIG. 4, the other end of the connecting member 797 may abut a step unit between the small diameter part 810 and the large diameter part 820.

In the first assembling process, by connecting a wire connected to the substrate 745 to a display device in a state in which each of the members is mounted on the jig 800, a signal indicating a light reception result acquired by the light receiving unit 743b of the detecting unit 740 may be displayed on the display device. For example, by rotating the connecting member 797 around the central axis, a pulse waveform signal is displayed on the display device as the signal indicating the light reception result. Therefore, an operator may be notified of the signal indicating the light reception result.

Here, in a case in which a position and attitude of the sensor 743 with respect to the unit to be detected 730 are greatly different from a predetermined position and attitude, a ratio of a noise component in the signal indicating the light reception result may increase. When the ratio of the noise component in the signal indicating the light reception result is relatively large, detection precision of the rotation state of the unit to be detected 730 may be deteriorated. The predetermined position and attitude are a position and attitude of the sensor 743 with respect to the unit to be detected 730 at which the noise component in the signal indicating the light reception result is relatively reduced. The position and attitude of the sensor 743 with respect to the unit to be detected 730 vary in accordance with processing precision of the substrate 745, processing precision of the sensor 743, mounting precision of the sensor 743 to the substrate 745, or the like.

According to the present embodiment, as described above, by using the jig 800, the operator may be notified of a pulse waveform signal indicating a light reception result by rotating the connecting member 797 around the central axis in the state in which each of the members are mounted on the jig 800 in the first assembling process. Therefore, by adjusting a position at which the detecting unit 740 is mounted with respect to the second housing 780 while checking the signal, the operator may make the position and attitude of the sensor 743 with respect to the unit to be detected 730 be close to the predetermined position and attitude. Accordingly, detection precision of the rotation state of the unit to be detected 730 may be more easily improved. In this way, the first assembling process may include a position alignment process in which position alignment between the detecting unit 740 and the second housing 780 is performed using the jig 800 to make the position and attitude of the sensor 743 with respect to the unit to be detected 730 to be close to the predetermined position and attitude.

(Second Assembling Process)

Figure 6:
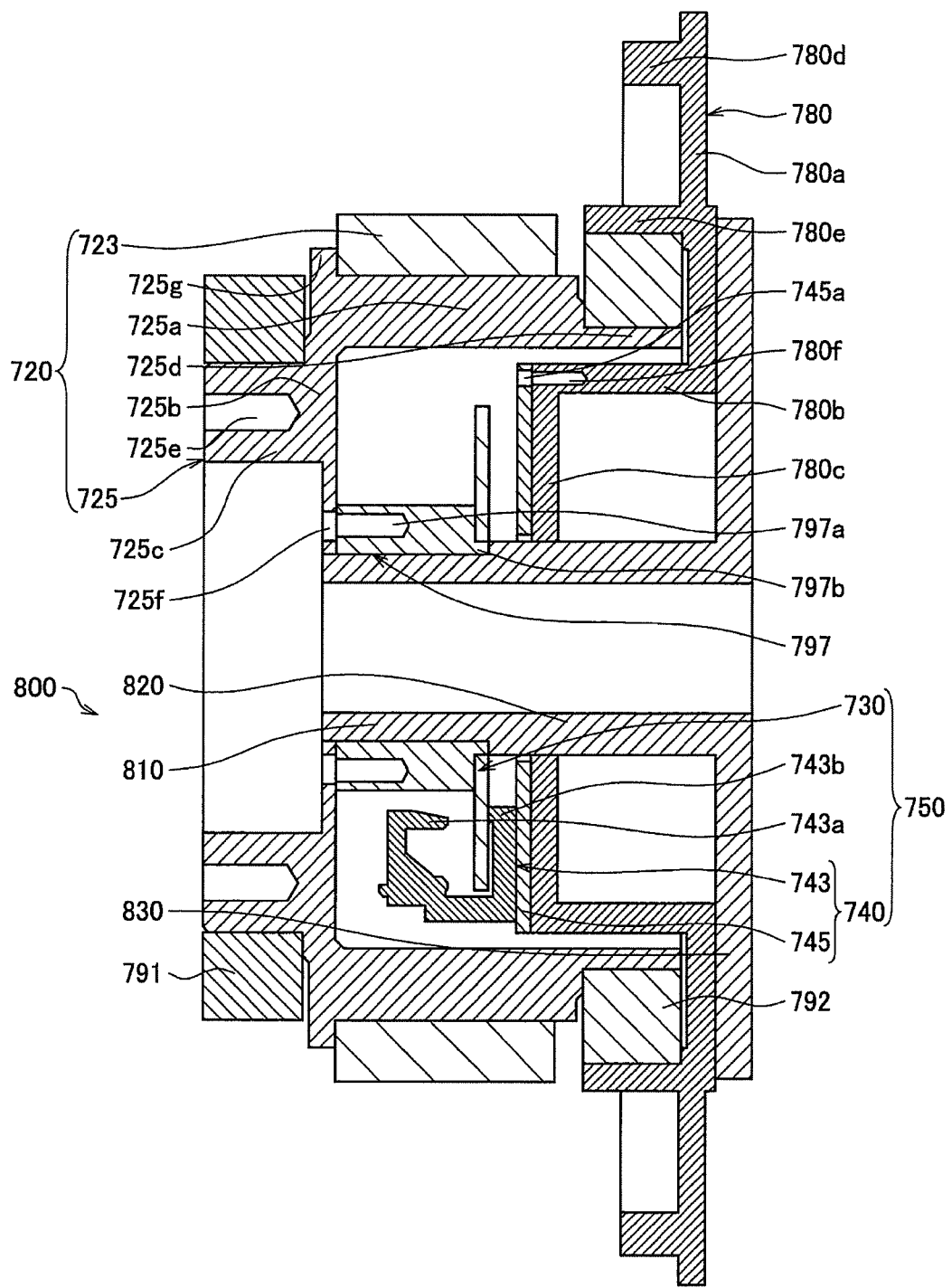
FIG. 6 is a cross-sectional diagram illustrating an example of an assembly including a rotor, a connecting member, an encoder, and a second housing assembled in a second assembling process.
Figure 7:
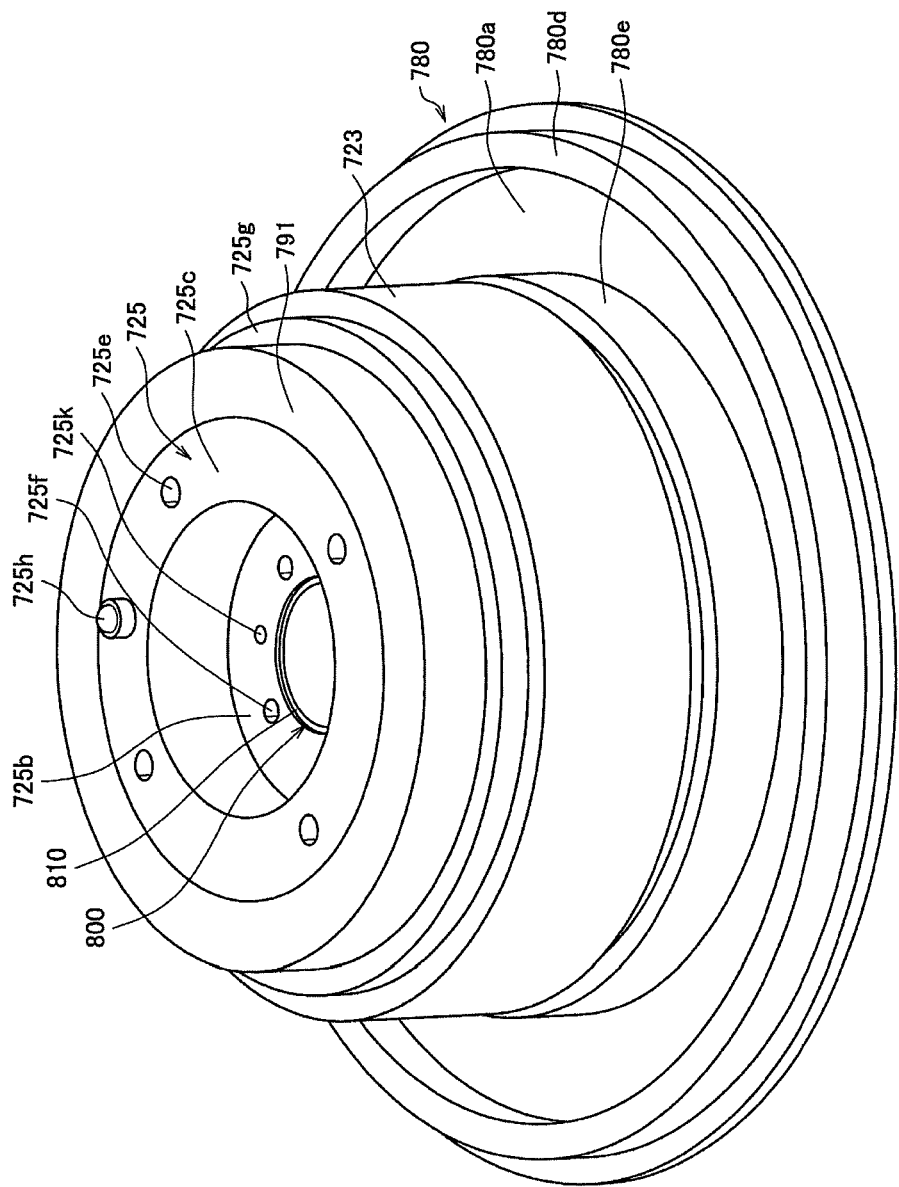
FIG. 7 is a perspective diagram illustrating the example of the assembly including the rotor, the connecting member, the encoder, and the second housing assembled in the second assembling process.

Next, the second assembling process will be described with reference to FIGS. 6 and 7. FIG. 6 is a cross-sectional diagram illustrating an example of an assembly including the rotor 720, the connecting member 797, the encoder 750, and the second housing 780 assembled in the second assembling process. FIG. 7 is a perspective diagram illustrating the example of the assembly including the rotor 720, the connecting member 797, the encoder 750, and the second housing 780 assembled in the second assembling process.

In the second assembling process, the rotor 720 is mounted on the assembly illustrated in FIG. 5 including the connecting member 797, the encoder 750, and the second housing 780 assembled in the first assembly process. Specifically, as illustrated in FIG. 6, mounting of the rotor 720 to the assembly is performed so that the base second protrusion 725d of the base 725 is fitted to the inner peripheral part of the second bearing 792, and the other end side of the inner peripheral part of the base second extension 725b of the base 725 and the one end of the connecting member 797 are opposite each other. As illustrated in FIG. 6, mounting of the rotor 720 to the assembly is performed so that the inner peripheral part of the base second extension 725b of the base 725 is fitted to the outer peripheral part of the small diameter part 810 of the jig 800.

Here, as described above, the inner peripheral part of the connecting member 797 is fitted to the small diameter part 810 of the jig 800. In this way, the jig 800 can be fitted to the inner peripheral parts of the base second extension 725b and the connecting member 797. Specifically, the connecting member 797 and the unit to be detected 730 are connected to each other such that the central axes thereof are substantially the same. Therefore, dimension precision in alignment of the rotation axis of the rotor 720 and the central axis of the unit to be detected 730 may be more easily improved. The second assembling process corresponds to a alignment process in which alignment of the rotation axis of the rotor 720 and the central axis of the unit to be detected 730 is performed using the jig 800.

Specifically, in the second assembly process, the base 725 is mounted on the connecting member 797 by a screw being inserted into the screw insertion hole 725f of the base 725 and being screwed to the screw mounting hole 797a of the connecting member 797.

In FIG. 7, an exterior of the assembly including the rotor 720, the connecting member 797, the encoder 750, and the second housing 780 assembled in the second assembling process and the jig 800 are illustrated. As illustrated in FIG. 7, a protrusion 725h for determining a position of the external member with respect to the base first protrusion 725c when mounting the external member of the motor 70 to the base first protrusion 725c may be provided at the one end of the base first protrusion 725c of the base 725. A plurality of screw mounting holes 725e may be provided at intervals in the circumferential direction in the one end of the base first protrusion 725c. A plurality of screw insertion holes 725f may be provided at intervals in the circumferential direction in the inner peripheral part of the base second extension 725b. In the inner peripheral part of the base second extension 725b, a hole 725k that can be fitted with the protrusion 797d of the connecting member 797 that has been described with reference to FIG. 5 may be provided at a position corresponding to the protrusion 797d.

(Third Assembling Process)

Figure 8:
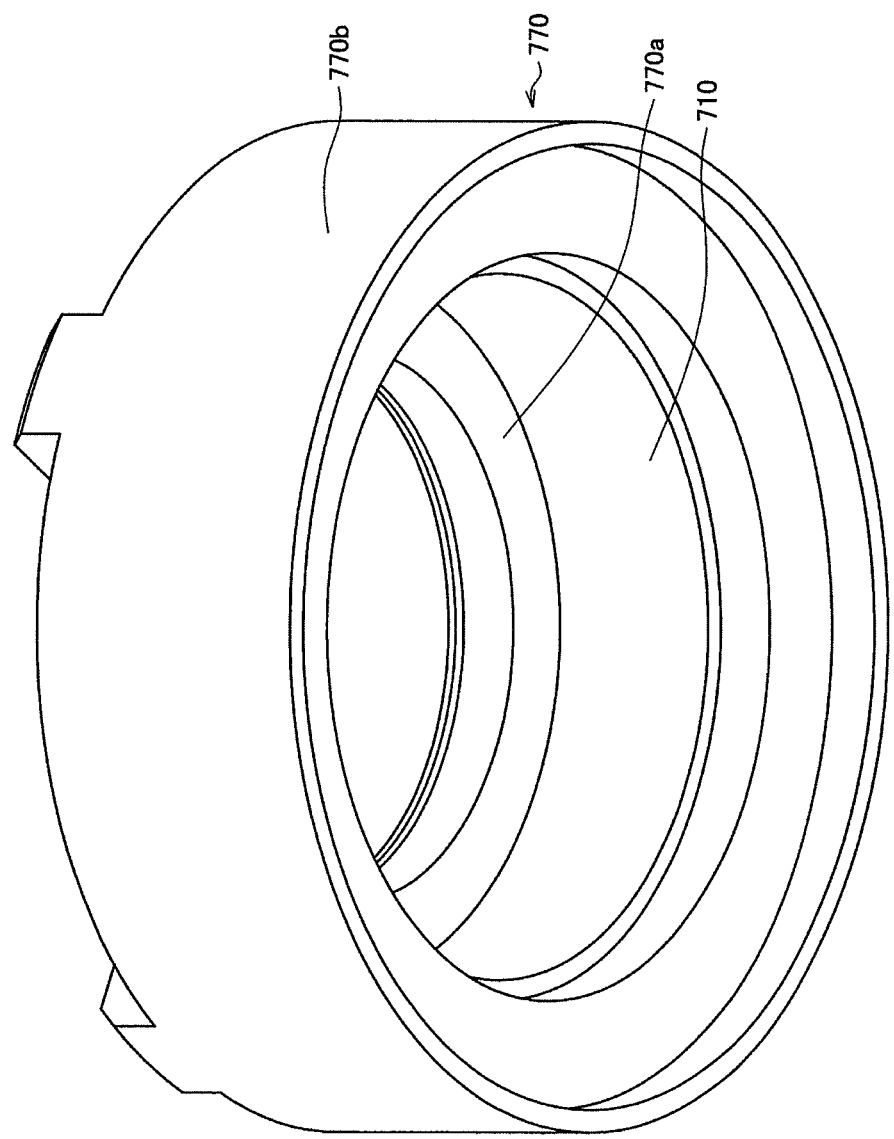
FIG. 8 is a perspective diagram illustrating an example of an assembly including a first housing and a stator assembled in a pre-assembling process.
Figure 9:
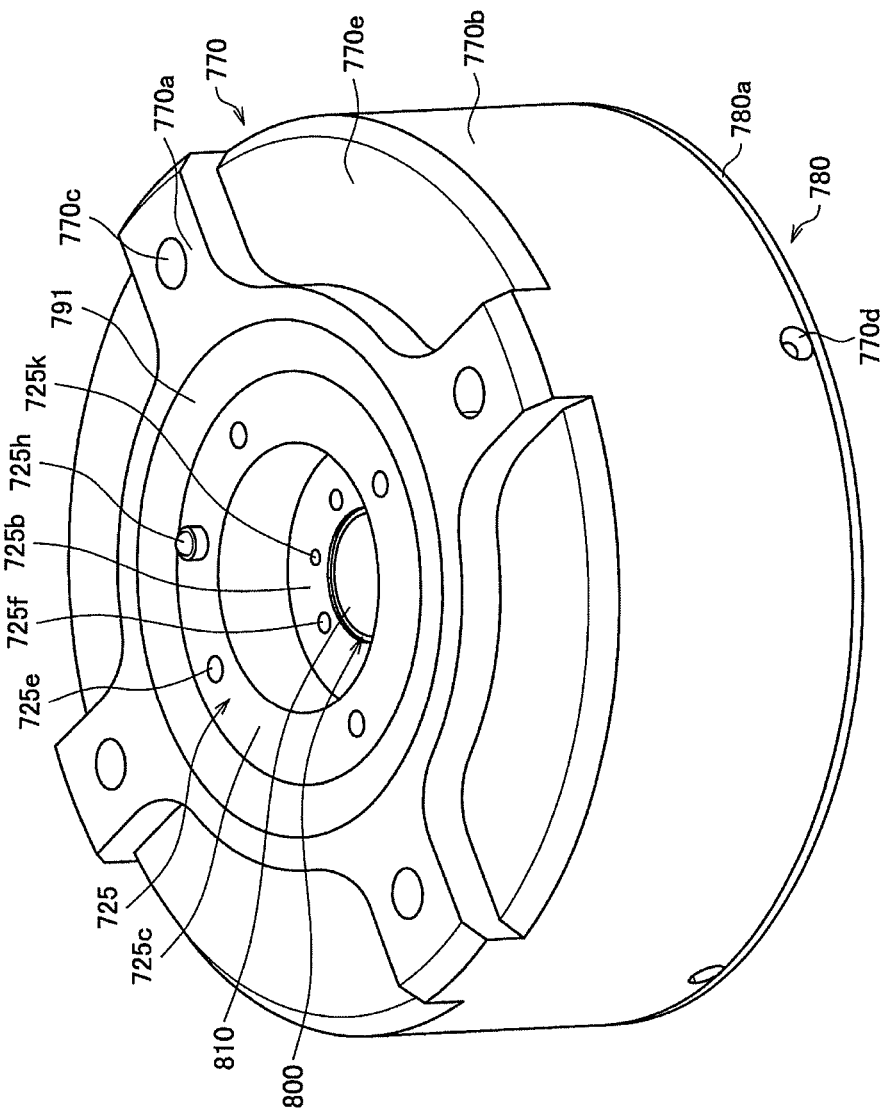
FIG. 9 is a perspective diagram illustrating an example of an assembly including a first housing, a stator, a rotor, a connecting member, an encoder, and a second housing assembled in a third assembling process.

Next, the third assembling process will be described with reference to FIGS. 8 and 9. FIG. 8 is a perspective diagram illustrating an example of an assembly including the first housing 770 and the stator 710 assembled in the pre-assembling process. FIG. 9 is a perspective diagram illustrating an example of an assembly including the first housing 770, the stator 710, the rotor 720, the connecting member 797, the encoder 750, and the second housing 780 assembled in the third assembling process.

In the third assembling process, the assembly illustrated in FIG. 8 including the first housing 770 and the stator 710 assembled in the pre-assembling process is mounted on the assembly illustrated in FIG. 7 including the rotor 720, the connecting member 797, the encoder 750, and the second housing 780 assembled in the second assembling process. Specifically, the mounting of the assembly illustrated in FIG. 8 to the assembly illustrated in FIG. 7 is performed such that that the other end of the first housing tubular unit 770b of the first housing 770 is fitted to the outer peripheral part of the second housing second tubular unit 780d of the second housing 780 and abuts one end side of the outer peripheral part of the annular disc unit 780a of the second housing 780. The mounting of the assembly illustrated in FIG. 8 to the assembly illustrated in FIG. 7 is performed such that the inner peripheral part of the first housing extension 770a of the first housing 770 is fitted to the outer peripheral part of the first bearing 791.

The jig 800 is separated from the assembly illustrated in FIG. 9 including the first housing 770, the stator 710, the rotor 720, the connecting member 797, the encoder 750, and the second housing 780 assembled in the third assembling process. As illustrated in FIG. 9, a plurality of screw mounting holes 770c may be provided at intervals in the circumferential direction at the one end of the first housing extension 770a. A thin wall unit 770e having a thin plate thickness in comparison to other portions may be formed at the one end of the first housing extension 770a for the purpose of reducing a weight of the motor 70. To improve a strength of a portion in the vicinity of the screw mounting hole 770c, preferably, the thin wall unit 770e is formed at a portion different from the portion in the vicinity of the screw mounting hole 770c. A screw insertion hole 770d that penetrates from the outer peripheral side to the inner peripheral side may be provided at the other end of the first housing tubular unit 770b of the first housing 770. For example, a screw mounting hole is provided at a position opposite to the screw insertion hole 770d of the first housing 770 in the second housing second tubular unit 780d of the second housing 780. Specifically, in the third assembling process, the second housing 780 is mounted on the first housing 770 by a screw being inserted into the screw insertion hole 770d of the first housing 770 and being screwed to the screw mounting hole of the second housing 780.

3. MODIFIED EXAMPLES

Next, motors according to various modified examples will be described with reference to FIGS. 10 to 13.

3-1. First Modified Example

Figure 10:
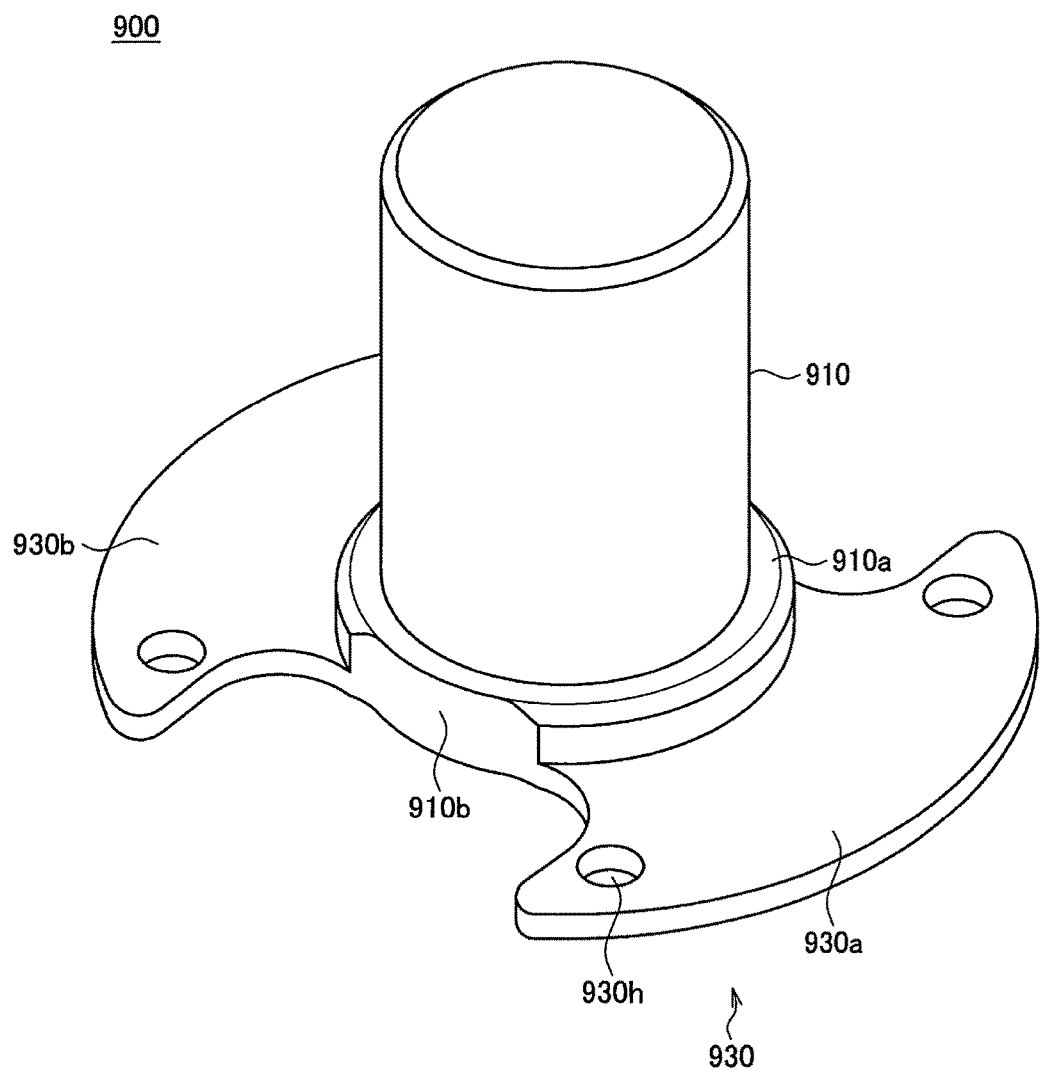
FIG. 10 is a perspective diagram for describing an example of a configuration of an insertion member according to a first modified example.
Figure 11:
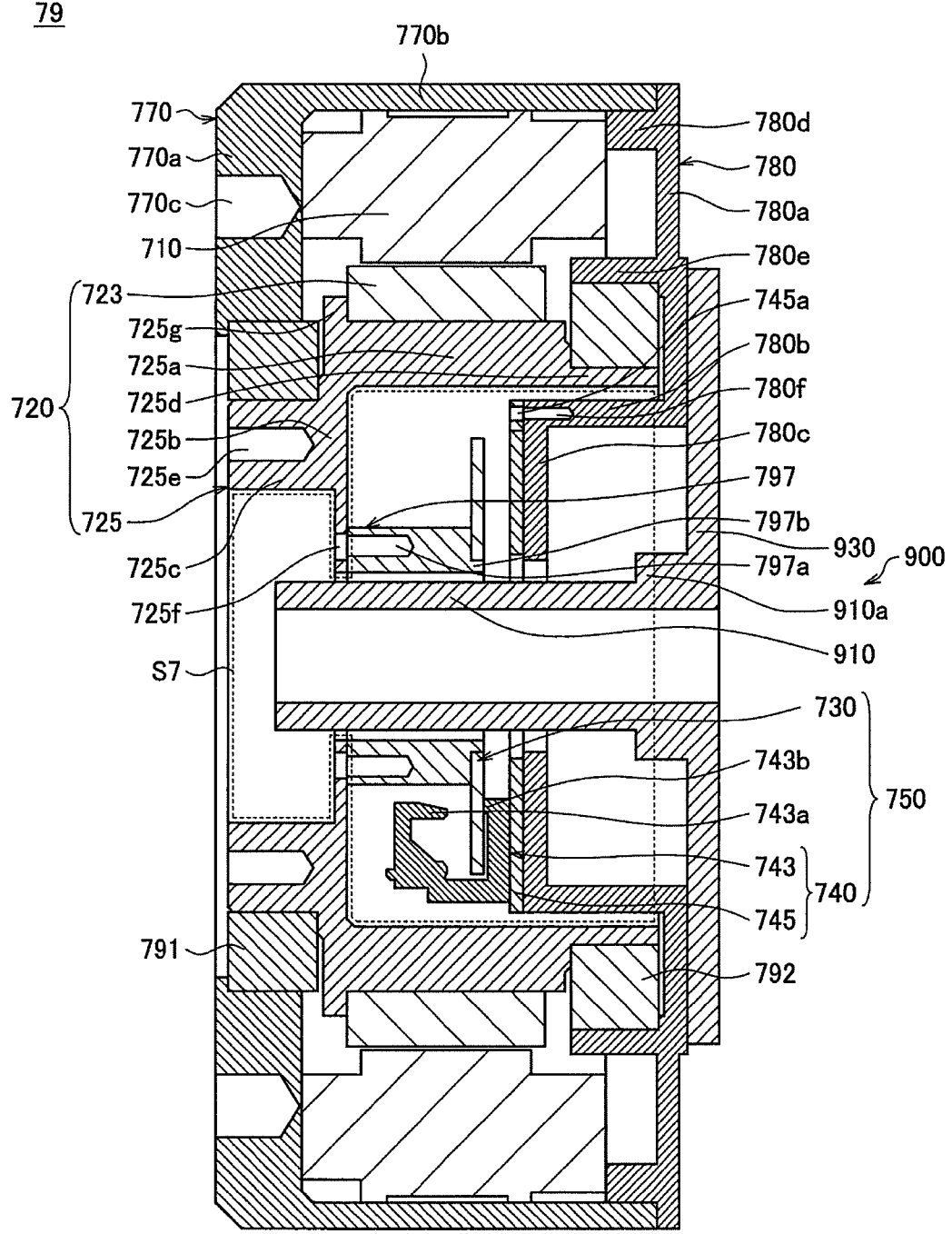
FIG. 11 is a cross-sectional diagram for describing an example of a configuration of a motor according to the first modified example.
Figure 12:
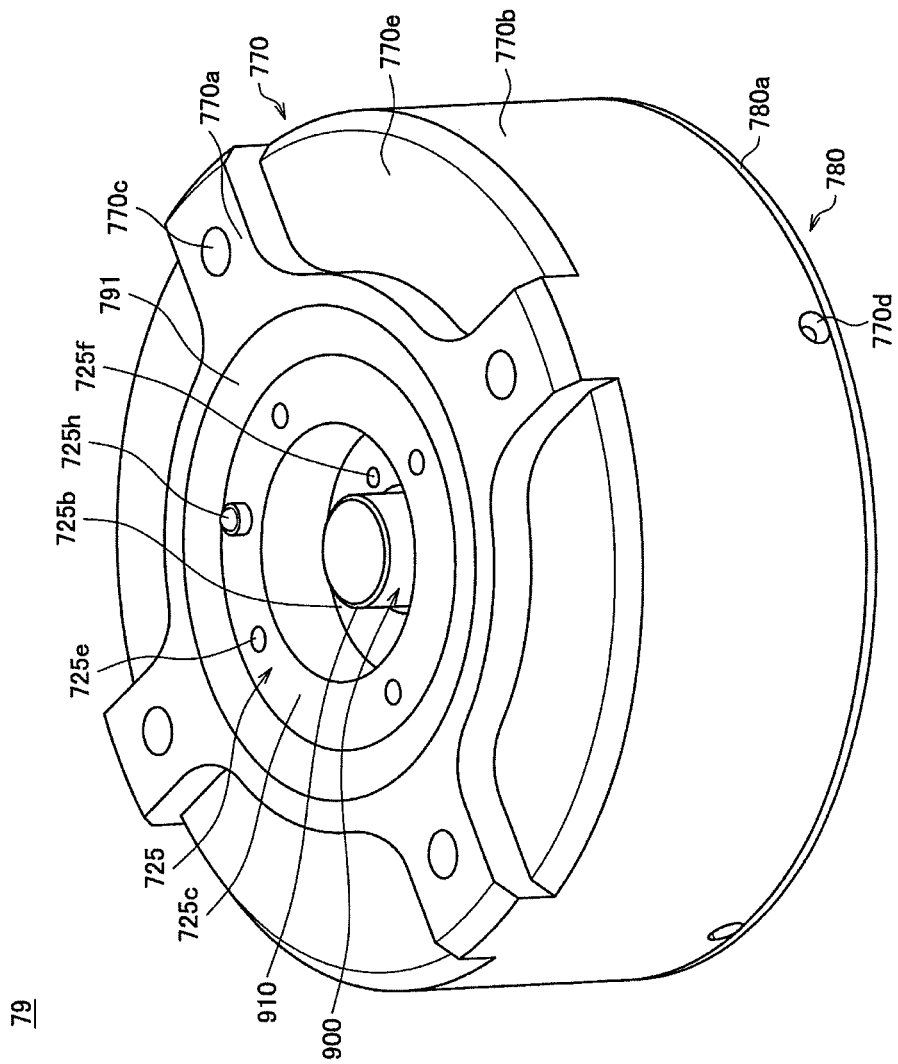
FIG. 12 is a perspective diagram for describing an example of the configuration of the motor according to the first modified example.

First, a motor 79 according to a first modified example will be described with reference to FIGS. 10 to 12. Unlike the motor 70 described with reference to FIG. 2, the motor 79 according to the first modified example includes an insertion member 900. FIG. 10 is a perspective diagram for describing an example of a configuration of the insertion member 900 according to the first modified example. FIG. 11 is a cross-sectional diagram for describing an example of a configuration of the motor 79 according to the first modified example. FIG. 12 is a perspective diagram for describing an example of a configuration of the motor 79 according to the first modified example.

The insertion member 900 may be configured with various metals such as aluminum or various resins such as nylon or PP. As illustrated in FIG. 10, the insertion member 900 includes an inserting unit 910 and an insertion member extension 930.

The inserting unit 910 is tubular. For example, as illustrated in FIG. 10, the inserting unit 910 is circularly tubular. As illustrated in FIG. 11, the inserting unit 910 is inserted into the inner peripheral sides of the base second extension 725b, the connecting member 797, the unit to be detected 730, the substrate 745, and the second housing extension 780c. A central axis of the inserting unit 910 may be substantially the same as rotation axis of the rotor 720. For example, an outer diameter of the inserting unit 910 is smaller than the inner diameters of the base second extension 725b, the connecting member 797, the unit to be detected 730, the substrate 745, and the second housing extension 780c. An axial length of the inserting unit 910 is longer than a distance between one end of the base second extension 725b and the other end of the second housing extension 780c. One end side of the inserting unit 910 has an opening, and the other end side thereof is connected to the insertion member extension 930. One end of the inserting unit 910 may be disposed at one end side or disposed at the other end side from the one end of the first housing extension 770a of the first housing 770.

The insertion member extension 930 extends from the other end of the inserting unit 910 toward the outer peripheral side. Specifically, as illustrated in FIG. 10, the insertion member extension 930 includes an insertion member first extension 930a extending from one side of the other end of the inserting unit 910 toward the outer peripheral side and an insertion member second extension 930b extending from the other side of the other end of the inserting unit 910 toward the outer peripheral side. For example, the insertion member first extension 930a and the insertion member second extension 930b are plate-shaped. Front ends of the insertion member first extension 930a and the insertion member second extension 930b have an arc shape arranged coaxially with the inserting unit 910 and protrude toward both sides in the circumferential direction.

A screw insertion hole 930h is provided in the insertion member first extension 930a and the insertion member second extension 930b. Specifically, in the front ends of the insertion member first extension 930a and the insertion member second extension 930b, the screw insertion hole 930h is provided at each of the portions protruding toward both of the sides in the circumferential direction. The screw insertion hole 930h is a so-called clearance hole that is provided for mounting the insertion member 900 on the second housing 780 and has an inner diameter larger than an outer diameter of a screw used in the mounting of the insertion member 900 to the second housing 780. When a countersunk screw is used as the screw, a part of the screw insertion hole 930h may have a shape corresponding to a head of the screw. Radial and circumferential positions at which the screw insertion holes 930h are provided in the insertion member 900 may be substantially the same as radial and circumferential positions at which the screw insertion holes 830h are provided in the jig 800.

A thick wall unit 910a having a thick plate thickness in comparison to other portions may be formed at the other end of the inserting unit 910. For example, an inner diameter of the thick wall unit 910a is same as the other portions in the inserting unit 910, and an outer diameter of the thick wall unit 910a is larger than the other portions in the inserting unit 910. Because the insertion member extension 930 extends from the other end of the inserting unit 910 toward the outer peripheral side, it is easy for stress to be concentrated on the other end of the inserting unit 910.

Therefore, a strength of the insertion member 900 can be improved by providing the thick wall unit 910a at the other end of the inserting unit 910. As illustrated in FIG. 10, the thick wall unit 910a may have a region 910b, whose outer diameter is small in comparison to other portions, at a portion in the circumferential direction.

As illustrated in FIG. 11, the insertion member extension 930 is connected to the other end of the second housing 780. Specifically, in the second housing 780, a screw mounting hole is provided at a position corresponding to the screw insertion hole 930h of the insertion member extension 930 illustrated in FIG. 10. When the radial and circumferential positions of the screw insertion holes 930h in the insertion member 900 and the screw insertion holes 830h in the jig 800 are substantially the same, the screw mounting hole provided in the second housing 780 may be used for both the mounting of the insertion member 900 and the mounting of the jig 800. The insertion member extension 930 is mounted on the other end of the second housing 780 by a screw being inserted into the screw insertion hole 930h of the insertion member extension 930 of the insertion member 900 and being screwed to the screw mounting hole of the second housing 780. Therefore, the insertion member 900 is mounted on the second housing 780.

Unlike the above-described method of manufacturing the motor 70, a method of manufacturing the motor 79 according to the first modified example includes a mounting process of mounting the insertion member 900 to the assembly including the first housing 770, the stator 710, the rotor 720, the connecting member 797, the encoder 750, and the second housing 780 assembled in the third assembly process. Specifically, after the above-described third assembling process, the motor 79 according to the first modified example is manufactured by removing the jig 800 from the assembly illustrated in FIG. 9 and mounting the insertion member 900 on the assembly.

As illustrated in FIG. 11, the through-hole that penetrates from one end side to the other end side and is arranged coaxially with the rotation axis of the rotor 720 is defined by an inner peripheral surface of the insertion member 900. Here, because the insertion member 900 is connected to the second housing 780, rotation of the insertion member 900 relative to the stator 710 is regulated. Therefore, when a wire connected to a device disposed around the motor 70 is inserted into the through-hole, contact between the wire and a portion of the motor 70 rotating with respect to the stator 710 can be prevented. Therefore, damage to the wire can be prevented.

3-2. Second Modified Example

Figure 13:
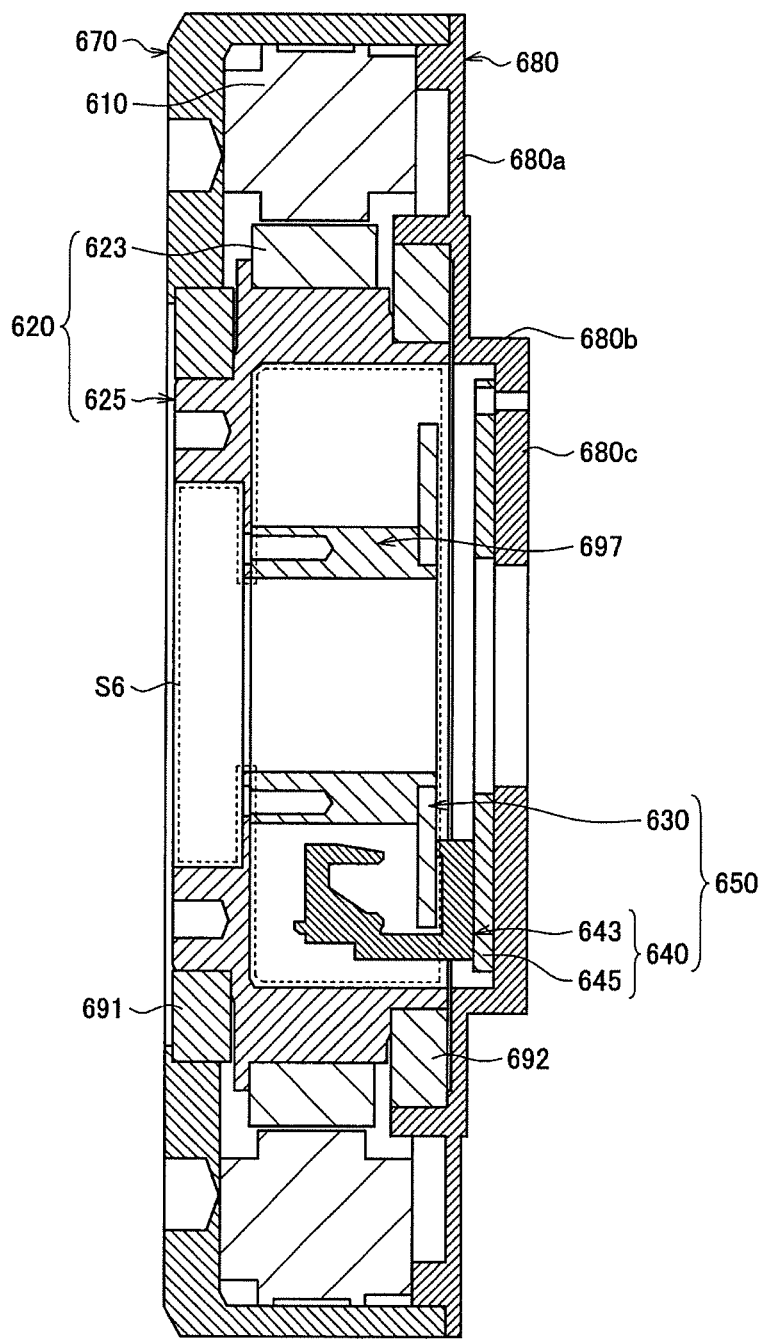
FIG. 13 is a cross-sectional diagram for describing an example of a configuration of a motor according to a second modified example.

Next, a motor 60 according to the second modified example will be described with reference to FIG. 13. In comparison to the motor 70 described with reference to FIG. 2, a ratio of a dimension of other members to a dimension of an encoder 650 is low in the motor 60 according to the second modified example. Unlike the motor 70 described with reference to FIG. 2, a second housing first tubular unit 680b in a second housing 680 protrudes in a reverse direction of a hollow space S6 side in the motor 60 according to the second modified example. FIG. 13 is a cross-sectional diagram for describing an example of a configuration of the motor 60 according to the second modified example.

A stator 610, a rotor 620, the encoder 650, and a first housing 670 in the motor 60 according to the second modified example have the same configurations as the stator 710, the rotor 720, the encoder 750, and the first housing 770, respectively, in the motor 70 described with reference to FIG. 2. A magnet unit 623 and a base 625 in the rotor 620 respectively correspond to the magnet unit 723 and the base 725 in the rotor 720. A unit to be detected 630 and a detecting unit 640 in the encoder 650 respectively correspond to the unit to be detected 730 and the detecting unit 740 in the encoder 750. A sensor 643 and a substrate 645 in the detecting unit 640 respectively correspond to the sensor 743 and the substrate 745 in the detecting unit 740. The hollow space S6 corresponds to the hollow space S7. The second housing 680 according to the second modified example has the same configuration as the second housing 780 except that the second housing first tubular unit 680b protrudes in the reverse direction of the hollow space S6 side.

Specifically, in comparison to the motor 70 described with reference to FIG. 2, a ratio of axial dimensions of the stator 610, the rotor 620, the first housing 670, and the second housing 680 to an axial dimension of the encoder 650 is low in the second modified example. Therefore, a part of the encoder 650 is disposed at the other end side from the other end of the base 625 in the second modified example. Specifically, a part of the sensor 643 and the substrate 645 of the encoder 650 are disposed at the other end side from the other end of the base 625. Accordingly, the part of the encoder 650 is disposed outside the hollow space S6 defined by the inner peripheral part of the rotor 720. Therefore, the second housing first tubular unit 680b in the second housing 680 protrudes in the reverse direction of the hollow space S6 side from an inner peripheral part of an annular disc unit 680a in the second modified example.

As described above, the portion of the encoder 650 is disposed outside the hollow space S6 in the second modified example. The other portion of the encoder 650 is disposed inside the hollow space S6. Therefore, like the motor 70 described with reference to FIG. 2, a portion provided at the inner peripheral side in comparison with the stator 610 and the rotor 620 can be effectively used as a portion in which the encoder 650 is provided. Accordingly, by providing the encoder 650 in the motor 60, an increase in dimension of the motor 60 can be prevented. Consequently, a size of the motor 60 can be further reduced. Accordingly, a size of a device in which the motor 60 is used can be effectively reduced.

4. APPLICATION EXAMPLES

Next, each of first and second application examples will be described with reference to FIGS. 14 to 16. The technology according to the present disclosure may be applied to various products. The first and second application examples described hereinafter are examples of application examples of the technology according to the present disclosure to various products.

4-1. First Application Example

First, the first application example will be described with reference to FIG. 14. The technology according to the present disclosure may be applied to an assist suit that is used by being worn by a person such as an elderly person who needs care and assists motion of the human body.

Figure 14:
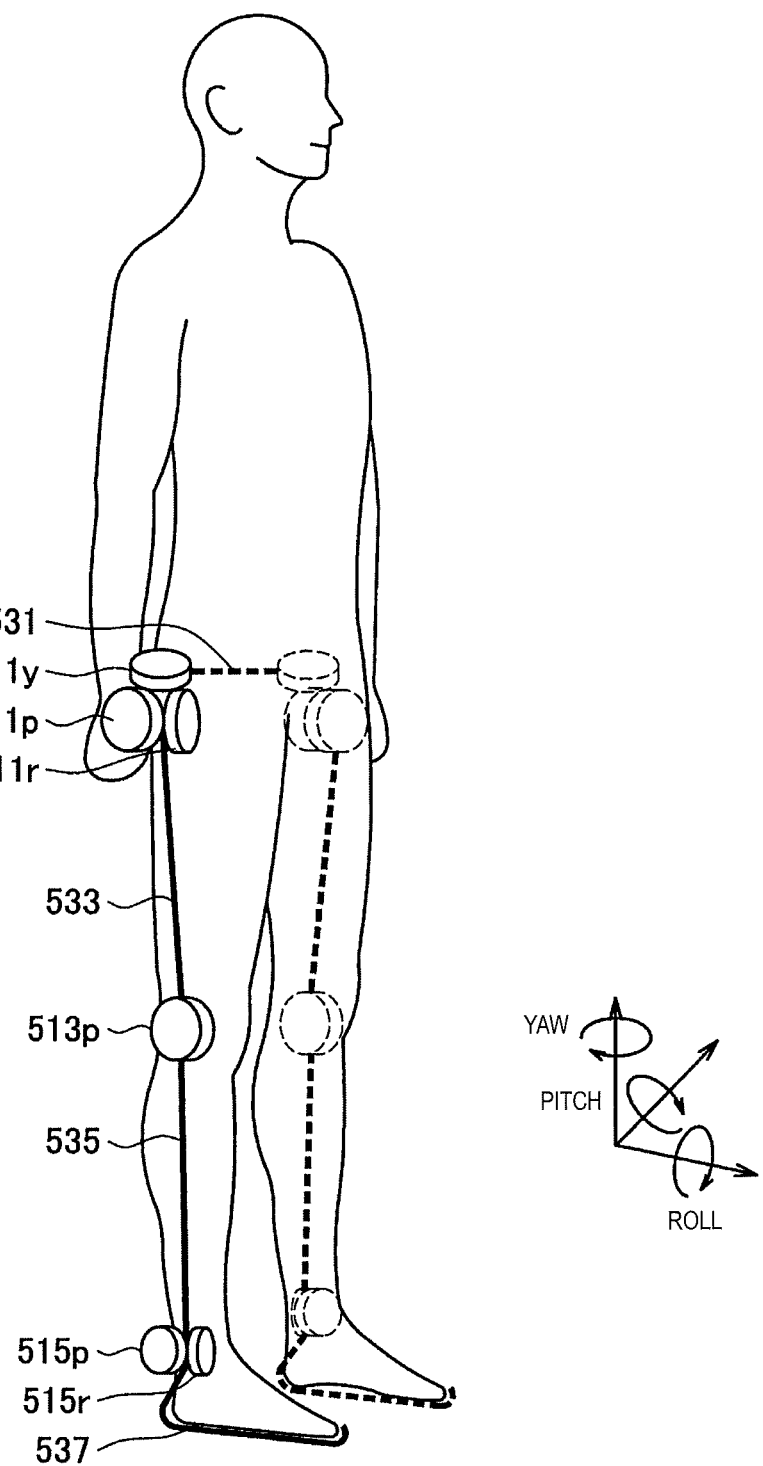
FIG. 14 is a diagram illustrating an example of a schematic configuration of an assist suit.

FIG. 14 is a diagram illustrating an example of a schematic configuration of an assist suit 5. Specifically, the assist suit 5 illustrated in FIG. 14 is worn on each leg of the human body and assists motion of each of the legs.

The assist suit 5 includes each actuator configured to generate torque around a joint axis with respect to a hip joint, a knee joint, and an ankle of left and right legs of the human body and each rigid body link configured to transmit the generated torques by connecting between each of the actuators. Specifically, as illustrated in FIG. 14, the assist suit 5 includes actuators 511y, 511p, and 511r provided in the vicinity of the hip joint, an actuator 513p provided in the vicinity of the knee joint, and actuators 515p and 515r provided in the vicinity of the ankle. The actuators are provided at each of the left and right legs.

As illustrated in FIG. 14, the assist suit 5 includes a pelvic link 531 configured to connect the actuators 511y, 511p, and 511r at the left leg side and the actuators 511y, 511p, and 511r at the right leg side, a femoral link 533 configured to connect the actuators 511y, 511p, and 511r and the actuator 513p, and a shank link 535 configured to connect the actuator 513p and the actuators 515p and 515r. As illustrated in FIG. 14, the assist suit 5 includes a sole link 537 passing through a sole from the actuators 515p and 515r and extending toward a toe of the leg. Each of the pelvic link 531, the femoral link 533, the shank link 535, and the sole link 537 may be fixed to the human body by a band (not illustrated).

Here, the actuators 511y, 511p, and 511r may respectively output torques around a yaw axis, a pitch axis, and a roll axis corresponding to the joint axis of the hip joint. The actuator 513p may output torque around a pitch axis corresponding to the joint axis of the knee joint. The actuators 515p and 515r may respectively output torques around a pitch axis and a roll axis corresponding to the joint axis of the ankle.

A control device (not illustrated) for controlling driving of each of the actuators is provided in the assist suit 5. For example, the control device may be provided in the vicinity of a pelvic unit. It may be configured so that the driving of each of the actuators is controlled on the basis of an operation instruction output from the control device. Specifically, the control device outputs a command value of a joint angle or joint angular velocity with respect to each of the joints as an operation instruction to the actuators, and the driving of each of the actuators is controlled so that an actual value of the joint angle or joint angular velocity becomes close to the command value.

For example, each of the actuators includes a motor, an encoder capable of detecting a rotation state of a rotor of the motor is mounted in the motor, and a detection result is output from the encoder to the control device. A torque sensor for detecting output torque is mounted in each of the actuators, and a detection result is output from the torque sensor to the control device. A contact sensor for detecting a contact state between a sole and a road surface is provided in each of the left and right sole units, and a detection result is output from the contact sensor to the control device. A ground measurement switch that is turned on when the sole is in contact with the road surface and is turned off when the sole is spaced apart from the road surface may be used in the contact sensor. An inertia measuring device including a three-axis acceleration sensor and a three-axis angular velocity sensor (for example, a gyro sensor) is provided in the pelvic unit, and a detection result is output from the inertia measuring device to the control device. The control device may control the driving of each of the actuators on the basis of the detection result output from each of the devices.

The technology according to the present disclosure can be properly applied to the motor included in each of the actuators 511y, 511p, 511r, 513p, 515p, and 515r among the configurations described above. A size of each of the actuators can be further reduced by applying the technology according to the present disclosure to the motor of each of the actuators. Further, a size of the assist suit 5 can be effectively reduced. Weights of each of the actuator and the assist suit 5 can be reduced.

4-2. Second Application Example

Next, the second application example will be described with reference to FIGS. 15 and 16. The technology according to the present disclosure may also be applied to a microscopic operation system that is used in so-called microsurgery performed by magnifying and observing a fine region of a patient.

Figure 15:
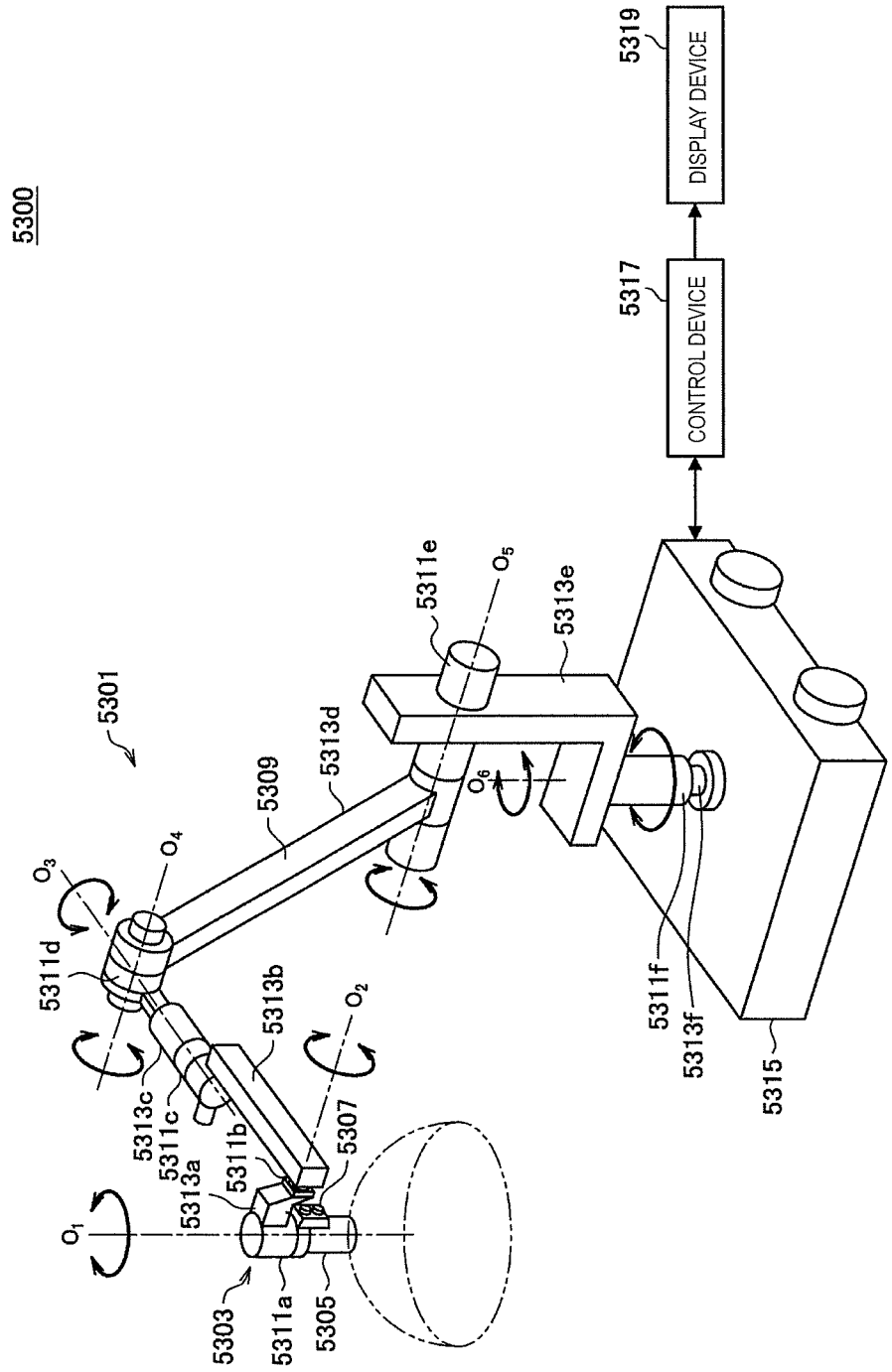
FIG. 15 is a diagram illustrating an example of a schematic configuration of a microscopic operation system

FIG. 15 is a diagram illustrating an example of a schematic configuration of a microscopic operation system 5300 to which the technology according to the present disclosure is applicable. Referring to FIG. 15, the microscopic operation system 5300 is configured with a microscope device 5301, a control device 5317, and a display device 5319. In the following description of the microscopic operation system 5300, "user" refers to arbitrary medical staff such as an operator and an assistant who uses the microscopic operation system 5300.

The microscope device 5301 has a microscope unit 5303 for enlarging and observing an observation object (an operating site of a patient), an arm unit 5309 that supports the microscope unit 5303 at its leading end, and a base unit 5315 that supports a base end of the arm unit 5309.

The microscope unit 5303 is made up of an approximately cylindrical barrel unit 5305, an imaging unit (not illustrated) provided inside the barrel unit 5305, and an operating unit 5307 provided in a partial region on the outer circumference of the barrel unit 5305. The microscope unit 5303 is an electronic imaging microscope unit (also known as a video microscope unit) that images a captured image electronically with the imaging unit.

The aperture on the bottom end of the barrel unit 5305 is provided with a cover glass that protects the imaging unit inside. Light from the observation target (hereinafter also called observation light) passes through the cover glass and is incident on the imaging unit inside the barrel unit 5305. Note that a light source made up of a light-emitting diode (LED) or the like, for example, may also be provided inside the barrel unit 5305, and during imaging, light may be radiated from the light source onto the observation target through the cover glass.

The imaging unit is made up of an optical system that condenses observation light, and an image sensor that senses the observation light condensed by the optical system. The optical system is made up of a combination of multiple lenses, including a zoom lens and a focus lens, the optical characteristics of which are adjusted so that an image of the observation light is formed on the light-sensitive face of the image sensor. The image sensor senses and photoelectrically converts the observation light to thereby generate a signal corresponding to the observation light, or in other words, an image signal corresponding to the observed image. A sensor capable of color photography including a Bayer array, for example, is used as the image sensor. The image sensor may be any of various known types of image sensors, such as a complementary metal-oxide-semiconductor (CMOS) image sensor or a charge-coupled device (CCD) image sensor. The image signal generated by the image sensor is transmitted to the control device 5317 as RAW data. At this point, the transmission of the image signal may be conducted favorably by optical communication. This is because at the surgery venue, the surgeon performs surgery while observing the state of the affected area via the captured image, and thus for safer and more reliable surgery, there is demand for the moving image of the operating site to be displayed as close to real-time as possible. Transmitting the image signal by optical communication makes it possible to display the captured image with low latency.

Note that the imaging unit may also include a drive mechanism that moves the zoom lens and the focus lens of the optical system along the optical axis. By suitably moving the zoom lens and the focus lens with the drive mechanism, the magnification factor of the captured image and the focus distance during imaging may be adjusted. Also, the imaging unit may be provided with any of various types of functions typically provided in electronic imaging microscope units, such as an auto exposure (AE) function, an auto focus (AF) function or the like.

In addition, the imaging unit may be configured as a so-called one-chip imaging unit that includes a single image sensor, or as a so-called multi-chip imaging unit that includes multiple image sensors. If the imaging unit has a multi-chip configuration, image signals corresponding to R, G, and B are generated by respective image sensors, for example, and a color image may be obtained by combining these image signals. Alternatively, the imaging unit may be configured to include a pair of image sensors for respectively acquiring image signals for the right eye and the left eye corresponding to stereoscopic vision (3D display). By presenting a 3D display, the surgeon becomes able to grasp the depth of biological tissue in the operating site more accurately. Note that if the imaging unit has a multi-chip configuration, the optical system is provided with multiple subsystems corresponding to each of the image sensors.

The operating unit 5307 is made up of elements such as a directional lever or switches, for example, and is an input unit that accepts operating input from a user. For example, via the operating unit 5307, the user is able to input an instruction to change the magnification factor of the observation target and the focus distance to the observation target.

By having the driving mechanism of the imaging unit suitably drive the zoom lens and the focus lens in accordance with the instruction, the magnification factor and the focus distance may be adjusted. As another example, via the operating unit 5307, the user is able to input an instruction to toggle the operating mode of the arm unit 5309 (an all-free mode and a locked mode described later). Note that when the user wants to move the microscope unit 5303, it is anticipated that the user moves the microscope unit 5303 by gripping and holding the barrel unit 5305. Consequently, the operating unit 5307 preferably is provided at a position that allows easy operation with the fingers while the user is gripping the barrel unit 5305, to thereby allow the user to operate the operating unit 5307 even while moving the barrel unit 5305.

The arm unit 5309 is configured as a result of multiple links (a first link 5313*a* to a sixth link 5313*f*) being rotatably joined to each other by multiple joint units (a first joint unit 5311*a* to a sixth joint unit 5311*f*).

The first joint unit 5311*a* has an approximately cylindrical shape, and on the leading end (bottom end) thereof supports the top end of the barrel unit 5305 of the microscope unit 5303, so as to allow rotation about a rotation axis (first axis $O_1$) parallel to the central axis of the barrel unit 5305. Herein, the first joint unit 5311*a* may be configured so that the first axis $O_1$ is aligned with the optical axis of the imaging unit of the microscope unit 5303. Consequently, rotating the microscope unit 5303 about the first axis $O_1$ makes it possible to change the field of view as though rotating the captured image.

The first link 5313*a* securely supports the first joint unit 5311*a* on the leading end thereof. Specifically, the first link 5313*a* is an approximately L-shaped rod-like member, the leading edge of which extends in a direction orthogonal to the first axis $O_1$, while also being connected to the first joint unit 5311*a* so that the end of that edge abuts the top end on the outer circumference of the first joint unit 5311*a*. The second joint unit 5311*b* is connected to the end of the base edge of the approximate L-shape of the first link 5313*a*.

The second joint unit 5311*b* has an approximately cylindrical shape, and on the leading end thereof supports the base end of the first link 5313*a*, so as to allow rotation about a rotation axis (second axis $O_2$) orthogonal to the first axis $O_1$. The leading end of the second link 5313*b* is securely connected to the base end of the second joint unit 5311*b*.

The second link 5313*b* is an approximately L-shaped rod-like member, the leading edge of which extends in a direction orthogonal to the second axis $O_2$, while the end of that edge is securely connected to the base end of the second joint unit 5311*b*. The third joint unit 5311*c* is connected to the base edge of the approximate L-shape of the second link 5313*b*.

The third joint unit 5311*c* has an approximately cylindrical shape, and on the leading end thereof supports the base end of the second link 5313*b*, so as to allow rotation about a rotation axis (third axis $O_3$) orthogonal to both the first axis $O_1$ and the second axis $O_2$. The leading end of the third link 5313*c* is securely connected to the base end of the third joint unit 5311*c*. By rotating the configuration on the leading-end side, including the microscope unit 5303, about the second axis $O_2$ and the third axis $O_3$, the microscope unit 5303 may be moved to change the position of the microscope unit 5303 on the horizontal plane. In other words, controlling the rotation about the second axis $O_2$ and the third axis $O_3$ makes it possible to move the field of view of the captured image on a flat plane.

The third link 5313*c* is configured to have an approximately cylindrical shape on the leading end side, and on the leading end of the cylindrical shape, the base end of the third joint unit 5311*c* is securely connected so that both have approximately the same central axis. The base end side of the third link 5313*c* has a rectangular column shape, and the fourth joint unit 5311*d* is connected to the end thereof.

The fourth joint unit 5311*d* has an approximately cylindrical shape, and on the leading end thereof supports the base end of the third link 5313*c*, so as to allow rotation about a rotation axis (fourth axis $O_4$) orthogonal to the third axis $O_3$. The leading end of the fourth link 5313*d* is securely connected to the base end of the fourth joint unit 5311*d*.

The fourth link 5313*d* is a rod-like member that extends approximately linearly in a direction orthogonal to the fourth axis $O_4$, while also being securely connected to the fourth joint unit 5311*d* so that the leading end abuts the side face of the approximately cylindrical shape of the fourth joint unit 5311*d*. The fifth joint unit 5311*e* is connected to the base end of the fourth link 5313*d*.

The fifth joint unit 5311*e* has an approximately cylindrical shape, and on the leading end side thereof supports the base end of the fourth link 5313*d*, so as to allow rotation about a rotation axis (fifth axis $O_5$) parallel to the fourth axis $O_4$. The leading end of the fifth link 5313*e* is securely connected to the base end of the fifth joint unit 5311*e*. The fourth axis $O_4$ and the fifth axis $O_5$ are rotation axes enabling the microscope unit 5303 to be moved in the vertical direction. By rotating the configuration on the leading-end side, including the microscope unit 5303, about the fourth axis $O_4$ and the fifth axis $O_5$, the height of the microscope unit 5303, or in other words the distance between the microscope unit 5303 and the observation target, may be adjusted.

The fifth link 5313*e* is made up of a combination of a first member having an approximate L-shape with one edge extending in the vertical direction while the other edge extends in the horizontal direction, and a rod-like second member that extends vertically downward from the unit of the first member that extends in the horizontal direction. The base end of the fifth joint unit 5311*e* is securely connected near the top end of the unit of the first member that extends in the vertical direction of the fifth link 5313*e*. The sixth joint unit 5311*f* is connected to the base end (bottom end) of the second member of the fifth link 5313*e*.

The sixth joint unit 5311*f* has an approximately cylindrical shape, and on the leading end side thereof supports the base end of the fifth link 5313*e*, so as to allow rotation about a rotation axis (sixth axis $O_6$) parallel to the vertical direction.

The leading end of the sixth link 5313*f* is securely connected to the base end of the sixth joint unit 5311*f*.

The sixth link 5313*f* is a rod-like member that extends in the vertical direction, with the base end securely connected to the top face of the base unit 5315.

The allowable rotation range of the first joint unit 5311*a* to the sixth joint unit 5311*f* is suitably set so that the microscope unit 5303 is capable of desired motion. Consequently, in the arm unit 5309 having the configuration described above, three degrees of translational freedom and three degrees of rotational freedom, for a total of six degrees of freedom, may be realized for the motion of the microscope unit 5303. In this way, by configuring the arm unit 5309 so that six degrees of freedom are realized for the motion of the microscope unit 5303, it becomes possible to freely control the position and the attitude of the microscope unit 5303 within the movable range of the arm unit 5309.

Consequently, it becomes possible to observe a operating site from any angle, and surgery may be executed more smoothly.

Note that the configuration of the arm unit 5309 illustrated in the diagram is merely one example, and factors such as the number and the shapes (lengths) of the links constituting the arm unit 5309, as well as the number and arrangement of the joint units and the directions of the rotation axes may be designed suitably so that the desired degrees of freedom may be realized. For example, as described above, to move the microscope unit 5303 freely, the arm unit 5309 preferably is configured to have six degrees of freedom, but the arm unit 5309 may also be configured to have more degrees of freedom (in other words, redundant degrees of freedom). When redundant degrees of freedom exist, in the arm unit 5309, it becomes possible to change the attitude of the arm unit 5309 while keeping the position and the attitude of the microscope unit 5303 in a locked state. Consequently, control that is more convenient to the surgeon, such as control of the attitude of the arm unit 5309 so that the arm unit 5309 does not interfere with the field of view of the surgeon looking at the display device 5319, for example, may be realized.

Herein, the first joint unit 5311*a* to the sixth joint unit 5311*f* may be provided with actuators equipped with a driving mechanism such as a motor, an encoder that detects the rotation angle in each joint unit, and the like. In addition, by having the control device 5317 suitable control the driving of each actuator provided for the first joint unit 5311*a* to the sixth joint unit 5311*f*, the attitude of the arm unit 5309, or in other words the position and the attitude of the microscope unit 5303, may be controlled. Specifically, the control device 5317 is able to ascertain the current attitude of the arm unit 5309 as well as the current position and attitude of the microscope unit 5303, on the basis of information about the rotation angle of each joint unit detected by the encoder. The control device 5317 uses the ascertained information to compute a control value for each joint unit (such as a rotation angle or a generated torque, for example) so that movement of the microscope unit 5303 corresponding to operation input from the user is realized.

Note that at this point, the method by which the control device 5317 controls the arm unit 5309 is not limited, and any of various known control methods, such as force control or position control, may be applied.

For example, by having the surgeon perform suitable operation input via an input device (not illustrated), the driving of the arm unit 5309 may be suitably controlled by the control device 5317 in accordance with the operation input, and the position and the attitude of the microscope unit 5303 may be controlled. By such control, after moving the microscope unit 5303 from an arbitrary position to an arbitrary position, the microscope unit 5303 may be supported securely at the new position. Note that with regard to the input device, in consideration of the surgeon's convenience, a device enabling operation even while the surgeon is holding surgical tools in his or her hands, such as a footswitch, for example, is preferably applied. Also, non-contact operation input may also be performed on the basis of gesture detection or line-of-sight detection using wearable device or a camera provided inside the operating room. Consequently, even a user belonging to a clean area becomes able to operate equipment belonging to an unclean area with a greater degree of freedom. Alternatively, the arm unit 5309 may be operated by what is called a master-slave method. In this case, the arm unit 5309 may be operated remotely by a user via an input device installed in a location separate from the operating room.

Also, if force control is applied, what is called power-assist control may also be conducted, in which external force is received from a user, and the actuators of the first joint unit 5311a to the sixth joint unit 5311f are driven so that the arm unit 5309 moves smoothly in response to the external force. As a result, when the user grasps the microscope unit 5303 to move the position directly, the microscope unit 5303 may be moved with comparatively light force. Consequently, it becomes possible to move the microscope unit 5303 more intuitively with a simpler operation, and user convenience may be improved.

In addition, the driving of the arm unit 5309 may be controlled so as to perform a pivot operation. Herein, a pivot operation refers to an operation of moving the microscope unit 5303 so that the optical axis of the microscope unit 5303 stays pointed at a certain point in a space (hereinafter called the pivot point). A pivot operation makes it possible to observe the same observation position from various directions, thereby making more detailed observation of the affected area possible. Note that if the microscope unit 5303 is configured not to be able to adjust the focus distance, the pivot operation is preferably performed in a state in which the distance between the microscope unit 5303 and the pivot point is fixed. In this case, it is sufficient to adjust the distance between the microscope unit 5303 and the pivot point to the locked focus distance of the microscope unit 5303. As a result, the microscope unit 5303 moves over the face of a hemisphere (schematically illustrated in FIG. 15) centered on the pivot point and having a radius corresponding to the focus distance, and clear captured images are obtained even if the observation direction is changed. On the other hand, if the microscope unit 5303 is configured to be able to adjust the focus distance, the pivot operation may be performed with a variable distance between the microscope unit 5303 and the pivot point. In this case, for example, the control device 5317 may calculate the distance between the microscope unit 5303 and the pivot point on the basis of information regarding rotation angles of the joint units detected by the encoder and automatically adjust the focus distance of the microscope unit 5303 on the basis of the calculation result.

Alternatively, in a case in which the microscope unit 5303 has the AF function, the focus distance may be automatically adjusted by the AF function each time the distance between the microscope unit 5303 and the pivot point changes due to a pivot operation.

In addition, the first joint unit 5311a to the sixth joint unit 5311f may also be provided with brakes that restrain rotation. The operation of such brakes may be controlled by the control device 5317. For example, when it is desirable to lock the position and the attitude of the microscope unit 5303, the control device 5317 applies the brake on each joint unit. As a result, the attitude of the arm unit 5309, or in other words the position and the attitude of the microscope unit 5303, may be locked without driving the actuators, and power consumption may be reduced. When it is desirable to move the position and the attitude of the microscope unit 5303, it is sufficient for the control device 5317 to release the brake on each joint unit and drive the actuators in accordance with a certain control method.

Such a brake operation may be performed in response to operation input performed by a user via the operating unit 5307 described above. When the user wants to move the position and the attitude of the microscope unit 5303, the user operates the operating unit 5307 to release the brake on each joint unit. As a result, the operating mode of the arm unit 5309 switches to a mode allowing each joint unit to be rotated freely (all-free mode). Meanwhile, when the user wants to lock the position and the attitude of the microscope unit 5303, the user operates the operating unit 5307 to apply the brake on each joint unit. As a result, the operating mode of the arm unit 5309 switches to a mode in which the rotation of each joint unit is restrained (locked mode).

The control device 5317 controls operations of the microscope device 5301 and the display device 5319, and thereby controls overall operations of the microscopic operation system 5300. For example, the control device 5317 controls the driving of the arm unit 5309 by causing the actuators of the first joint unit 5311a to the sixth joint unit 5311f to operate in accordance with a certain control method. As another example, the control device 5317 changes the operating mode of the arm unit 5309 by controlling the operation of the brakes of the first joint unit 5311a to the sixth joint unit 5311f. As another example, the control device 5317 performs various types of signal processing on an image signal acquired by the imaging unit of the microscope unit 5303 in the microscope device 5301, and also makes the image data to be displayed on the display device 5319. For the signal processing, any of various known types of signal processing, such as a development process (demosaicing process), an image quality-improving process (such as a band enhancement process, a super-resolution process, a noise reduction (NR) process, and/or a shake correction process), and/or an enlargement process (that is, a digital zoom process), may be performed.

Note that the communication between the control device 5317 and the microscope unit 5303, as well as the communication between the control device 5317 and the first joint unit 5311a to the sixth joint unit 5311f, may be wired communication or wireless communication. In the case of wired communication, communication using electrical signals may be conducted, or optical communication may be conducted. In this case, the transmission cable used for wired communication may be configured as an electrical signal cable, optical fiber, or a composite cable of the two, in accordance with the communication method. Meanwhile, in the case of wireless communication, it is no longer necessary to lay down a transmission cable inside the operating room, and thus a situation in which the movement of medical staff inside the operating room is impeded by such a transmission cable may be resolved.

The control device 5317 may be a processor such as a central processing unit (CPU) or a graphics processing unit (GPU), a micro computer or a control board on which a processor and a storage element such as a memory are both mounted, or the like. As a result of the processor of the control device 5317 operating in accordance with a certain program, the various functions described above may be realized. Note that, in the example illustrated in the diagram, the control device 5317 is provided as a separate device from the microscope device 5301, but the control device 5317 may also be unified with the microscope device 5301, such as by being installed inside the base unit 5315 of the microscope device 5301, for example. Alternatively, the control device 5317 may be made up of multiple devices. For example, by disposing a micro-computer, a control board or the like in the microscope unit 5303 and each of the first joint unit 5311a to the sixth joint unit 5311f of the arm unit 5309, and communicably connecting these control boards to each other, functions similar to the control device 5317 may be realized.

The display device 5319 displays an image corresponding to image data generated by the control device 5317 provided in an operating room under control of the control device 5317. That is, the display device 5319 displays an image of an operating site photographed by the microscope unit 5303 thereon. Note that the display device 5319 may also display various kinds of information regarding the operation, for example, physical information of the patient or an operative procedure, instead of or along with the image of the operating site. In this case, the display of the display device 5319 may be appropriately switched according to a manipulation of the user. Alternatively, a plurality of display devices 5319 may be provided, and the plurality of display devices 5319 may respectively display the image of the operating site and the various kinds of information regarding the operation. Any of various known types of display devices, such as a liquid crystal display device or an electroluminescence (EL) display device, for example, may be applied as the display device 5319.

Figure 16:
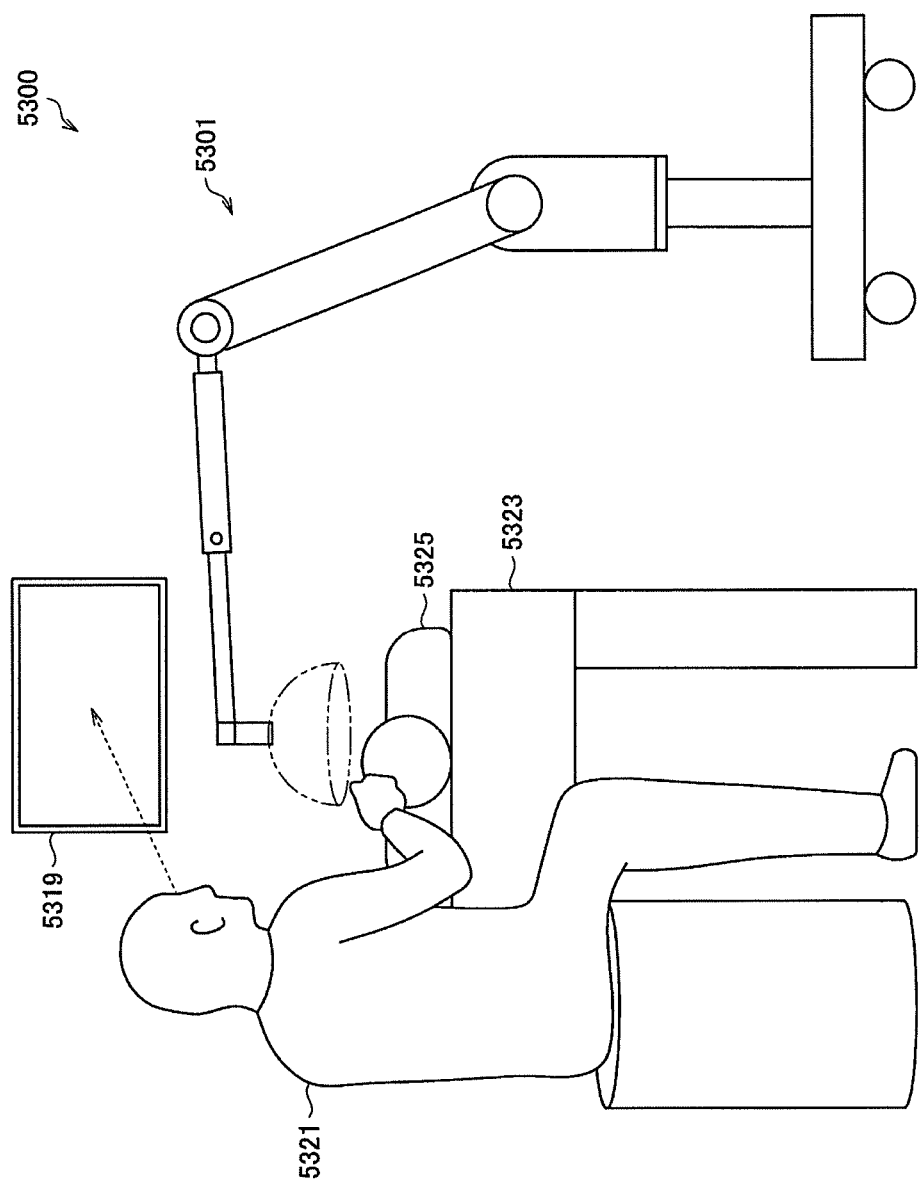
FIG. 16 is a diagram illustrating a state of an operation in which the microscopic operation system illustrated in FIG. 15 is being used.

FIG. 16 is a diagram illustrating a state of an operation in which the microscopic operation system 5300 illustrated in FIG. 15 is being used. FIG. 16 schematically illustrates the state in which an operator 5321 is performing an operation with respect to a patient 5325 lying on a patient bed 5323, using the microscopic operation system 5300. Note that, in FIG. 16, illustration of the control device 5317 is omitted from the configuration of the microscopic operation system 5300 and simplified illustration of the microscope device 5301 is shown for the sake of simplicity.

As illustrated in FIG. 16, an enlarged image of an eye, which is an operating site, photographed by the microscope device 5301 is displayed on the display device 5319 installed on a wall of an operating room using the microscopic operation system 5300 during an operation. The display device 5319 is provided at a position opposite to the operator 5321, and, while observing a state of the operating site by an image projected on the display device 5319, the operator 5321 performs various treatments, such as excision of an affected area, on the operating site.

An example of the microscopic operation system 5300 to which the technology according to the present disclosure is applicable has been described above. Here, although the microscopic operation system 5300 has been described as an example, the system to which the technology according to the present disclosure is applicable is not limited to the example. For example, the microscope device 5301 can also function as a support arm device that supports an observation device or a surgical tool other than the microscope unit 5303 at the front end thereof. For example, an endoscope may be applied as the other observation device. Forceps, tweezers, a pneumoperitoneum tube for pneumoperitoneum, or an energy treatment tool for performing incision of the tissue or sealing of the blood vessel by cauterization may be applied as the other surgical tool. By supporting the observation device or surgical tool by the support arm device, a position of the observation device or surgical tool can be more stably fixed in comparison to the case in which the medical staff supports the observation device or surgical tool by hand, and the burden on the medical staff can be reduced. The technology according to the present disclosure may also be applied to the support arm device that supports a configuration other than the microscope unit.

The technology according to the present disclosure can be properly applied to a motor provided in an actuator provided in the first joint unit 5311*a* to the sixth joint unit 5311*f* among the configurations described above. By applying the technology according to the present disclosure to the motor provided in the actuator provided in each of the joint units, a size of the actuator provided in each of the joint units can be further reduced. Therefore, a size of each of the joint units can be further reduced. Accordingly, a size of the microscope device 5301 can be effectively reduced. Further, weights of each of the joint units and the microscope device 5301 can be reduced.

5. CONCLUSION

As described above, according to an embodiment of the present disclosure, at least a part of the encoder 750 is disposed in the hollow space provided at the inner peripheral side in comparison with the stator 710 and the rotor 720. Therefore, a portion provided at the inner peripheral side in comparison with the stator 710 and the rotor 720 can be effectively used as the portion in which the encoder 750 is provided. Accordingly, an increase in dimension of the motor 70 can be prevented by providing the encoder 750 in the motor 70. Consequently, a size of the motor 70 can be further reduced. Accordingly, a size of the device can be effectively reduced. Further, weights of the motor 70 and the device using the motor 70 may be reduced.

Although the example in which the rotor 720 is disposed at the inner peripheral side in comparison with the stator 710 has been described in the above description, the technology according to the present disclosure may also be applied to a motor in which a rotor is disposed at the outer peripheral side in comparison with a stator. In that case, a hollow space may be defined by an inner peripheral part of the stator. At least a part of an encoder is configured to be disposed in the hollow space defined by the inner peripheral part of the stator.

Although the example in which the motor 70 is a brushless DC motor has been described in the above description, the type of motor to which the technology according to the present disclosure is applicable is not particularly limited. For example, a motor to which the technology according to the present disclosure is applicable may be a motor having a brush and a commutator. A power supply of a motor to which the technology according to the present disclosure is applicable may be a DC power supply, a single phase AC power supply, or a three-phase AC power supply. A motor to which the technology according to the present disclosure is applicable may also be a stepping motor.

Although the example in which the encoder 750 is an optical encoder using transmission of light has been described in the above description, the type of encoder to which the technology according to the present disclosure is applicable is not particularly limited. For example, an encoder to which the technology according to the present disclosure is applicable may be an optical encoder using reflection of light. In that case, a region that reflects radiated light and a region that absorbs or irregularly reflects the light are alternately provided in the circumferential direction of the rotor in the unit to be detected, and the light receiving unit of the detecting unit is provided at the radiating unit side with respect to the unit to be detected. An encoder to which the technology according to the present disclosure is applicable may be magnetic. An encoder to which the technology according to the present disclosure is applicable may be an incremental encoder or an absolute encoder.

Although the example in which the unit to be detected 730 is provided to be integrally rotatable with the rotor 720, and rotation of the detecting unit 740 relative to the stator 710 is regulated has been described in the above description, it may also be configured so that the detecting unit 740 is provided to be integrally rotatable with the rotor 720, and rotation of the unit to be detected 730 relative to the stator 710 is regulated.

The preferred embodiment(s) of the present disclosure has/have been described above with reference to the accompanying drawings, whilst the present disclosure is not limited to the above examples. A person skilled in the art may find various alterations and modifications within the scope of the appended claims, and it should be understood that they will naturally come under the technical scope of the present disclosure.

Further, the effects described in this specification are merely illustrative or exemplified effects, and are not limitative. That is, with or in the place of the above effects, the technology according to the present disclosure may achieve other effects that are clear to those skilled in the art from the description of this specification.

Additionally, the present technology may also be configured as below.

(1)
A motor including:
a stator;
a rotor that is provided to oppose the stator via a clearance; and
an encoder that is capable of detecting a rotation state of the rotor, in which a hollow space is provided at an inner peripheral side in comparison with the stator and the rotor, and
at least a part of the encoder is disposed in the hollow space.

(2)
The motor according to (1), including
a through-hole that penetrates from one end side to the other end side and that is arranged coaxially with a rotation axis of the rotor.

(3)
The motor according to (2), in which
the rotor is disposed at an inner peripheral side in comparison with the stator, and
the hollow space is defined by an inner peripheral part of the rotor.

(4)
The motor according to (3), in which
the encoder includes a unit to be detected and a detecting unit capable of detecting a rotation state of the unit to be detected,
the unit to be detected is provided to be integrally rotatable with the rotor, and
a rotation of the detecting unit relative to the stator is regulated.

(5)
The motor according to (4), in which
a light transmitting part that transmits radiated light and a light shielding part that shields the radiated light are alternately provided in a circumferential direction of the rotor in the unit to be detected,
a radiating unit that is capable of radiating light to the unit to be detected and a light receiving unit that is capable of receiving the light transmitted through the light transmitting unit are provided in the detecting unit, and
the detecting unit is capable of detecting the rotation state of the unit to be detected on the basis of a light reception result obtained by the light receiving unit.

(6)
The motor according to (4) or (5), in which
the unit to be detected is disc-shaped and has an opening at a center thereof,
the detecting unit includes a disc-shaped substrate having an opening at a center,
the substrate is provided to oppose the unit to be detected, and
the through-hole penetrates through inner peripheral sides of the unit to be detected and the substrate.

(7)
The motor according to (6), including:
a first housing that covers one end and an outer peripheral part of the stator and that is connected to the stator;
a second housing that covers the other end of the stator and that is connected to the first housing;
a tubular second housing tubular unit that is provided at a center of the second housing and that protrudes toward the hollow space;
a second housing extension that extends toward an inner peripheral side from one end of the second housing tubular unit;
a rotor extension that is provided at one end side of the rotor and that extends toward the inner peripheral side from an outer peripheral part; and
a tubular connecting member that connects the inner peripheral part of the unit to be detected and an inner peripheral part of the rotor extension,
in which the substrate of the detecting unit is oppositely connected to one end of the second housing extension, and
the through-hole penetrates inner peripheral sides of the rotor extension, the connecting member, and the second housing extension.

(8)
The motor according to (7), including
an insertion member that includes
a tubular inserting unit that is inserted into the inner peripheral sides of the rotor extension, the connecting member, the unit to be detected, the substrate, and the second housing extension, and
an insertion member extension that extends toward an outer peripheral side from the other end of the inserting unit and that is connected to the other end of the second housing,
in which the through-hole is defined by an inner peripheral surface of the insertion member.

(9)
The motor according to any one of (1) to (8), in which
the stator has a three-phase winding, and
the encoder detects a phase of a current flowing in the three-phase winding.

(10)
A motor manufacturing method including
an alignment process of aligning a rotation axis of a rotor and a central axis of a disc-shaped unit to be detected by using a jig that is capable of being fitted to inner peripheral parts of a rotor extension of a motor and a tubular connecting member,
in which the motor includes
a stator,
the rotor that is provided at an inner peripheral side in comparison with the stator to oppose the stator via a clearance,
a hollow space that is defined by an inner peripheral part of the rotor at the inner peripheral side in comparison with the rotor,
an encoder that includes the disc-shaped unit to be detected having an opening at a center thereof and a detecting unit that is capable of detecting a rotation state of the unit to be detected and that includes a disc-shaped substrate having an opening at a center thereof, the encoder being capable of detecting a rotation state of the rotor, a first housing that covers one end and an outer peripheral part of the stator and that is connected to the stator, a second housing that covers the other end of the stator and that is connected to the first housing, a tubular second housing tubular unit that is provided at a center of the second housing and that protrudes toward the hollow space, a second housing extension that extends toward the inner peripheral side from one end of the second housing tubular unit, the rotor extension that is provided at one end side of the rotor and that extends toward the inner peripheral side from an outer peripheral part, the tubular connecting member that connects an inner peripheral part of the unit to be detected and an inner peripheral part of the rotor extension, and a through-hole that penetrates from one end side to the other end side and that is arranged coaxially with a rotation axis of the rotor, and in which at least a part of the encoder is disposed in the hollow space, the substrate is provided opposite the unit to be detected and oppositely connected to one end of the second housing extension, and the through-hole penetrates inner peripheral sides of the rotor extension, the connecting member, the unit to be detected, the substrate, and the second housing extension.

(11)

The motor manufacturing method according to (10), including a position alignment process of aligning positions of the detecting unit and the second housing by using the jig, in which the jig is capable of being fitted to inner peripheral parts of the connecting member and the second housing extension.

(12)

The motor manufacturing method according to (10) or (11), including:

an assembling process of assembling an assembly including the stator, the rotor, the encoder, the first housing, the second housing, and the connecting member in a state in which the jig is installed; and a mounting process of removing, after the assembling process, the jig from the assembly and mounting an insertion member to the assembly, the insertion member including a tubular inserting unit that is inserted into inner peripheral sides of the rotor extension, the connecting member, the unit to be detected, the substrate, and the second housing extension and an insertion member extension that extends toward an outer peripheral side from the other end of the inserting unit and that is connected to the other end of the second housing.

REFERENCE SIGNS LIST 1 support device
5 assist suit
21, 22 rotating shaft
24, 26, 28, 30, 32, 34 shaft unit
41, 42, 44, 46, 47, 48 link
50 link mechanism
60, 70, 79 motor
80 noncircular gear
511y, 511p, 511r, 513p, 515p, 515r actuator
531 pelvic link
533 femoral link
535 shank link
537 sole link
710, 610 stator
720, 620 rotor
723, 623 magnet unit
725, 625 base
725a base tubular unit
725b second extension
725c first protrusion
725d second protrusion
725e screw mounting hole
725f screw insertion hole
725g first extension
725h protrusion
730, 630 part to be detected
730a light transmitting unit
730b light shielding unit
740, 640 detecting unit
743, 643 sensor
743a radiating unit
743b light receiving unit
745, 645 substrate
745a screw insertion hole
750, 650 encoder
770, 670 first housing
770a first housing extension
770b first housing tubular unit
770c screw mounting hole
770e thin wall unit
780, 680 second housing
780a, 680a annular disc unit
780b, 680b second housing first tubular unit
780c second housing extension
780d second housing second tubular unit
780e second housing third tubular unit
780f screw mounting hole
797 connecting member
797a screw mounting hole
797b connecting member protrusion
797c groove unit
800 jig
810 small diameter part
820 large diameter part
830 mounting unit
900 insertion member
910 inserting unit
930 insertion member extension
5300 microscopic operation system
5301 microscope device
5303 microscope unit
5305 barrel unit
5307 operating unit
5309 arm unit
5311a first joint unit
5311b second joint unit
5311c third joint unit
5311d fourth joint unit
5311e fifth joint unit
5311f sixth joint unit
5313a first link
5313b second link
5313c third link
5313d fourth link
5313e fifth link
5313f sixth link 5315 base unit
5317 control device
5319 display device

The invention claimed is:

1. A motor, comprising:
a stator;
a rotor that is provided to oppose the stator via a clearance, a hollow space being provided at an inner peripheral side in comparison with the stator and the rotor;
an encoder that detects a rotation state of the rotor, at least a part of the encoder being disposed in the hollow space;
a through-hole that penetrates from one end side to an other end side and that is arranged coaxially with a rotation axis of the rotor;
a first housing that covers one end and an outer peripheral part of the stator and that is connected to the stator;
a second housing that covers the other end of the stator and that is connected to the first housing;
a tubular second housing tubular unit that is provided at a center of the second housing and that protrudes toward the hollow space;
a second housing extension that extends toward an inner peripheral side from one end of the second housing tubular unit;
a rotor extension that is provided at one end side of the rotor and that extends toward the inner peripheral side from an outer peripheral part; and
a tubular connecting member that connects the inner peripheral part of the unit to be detected and an inner peripheral part of the rotor extension, wherein
the encoder includes a unit to be detected and a detecting unit that detects a rotation state of the unit to be detected,
the unit to be detected is disc-shaped and has an opening at a center thereof,
the detecting unit includes a disc-shaped substrate having an opening at a center,
the disc-shaped substrate is provided to oppose the unit to be detected,
the through-hole penetrates through inner peripheral sides of the unit to be detected and the substrate,
the disc-shaped substrate is oppositely connected to one end of the second housing extension, and
the through-hole penetrates inner peripheral sides of the rotor extension, the connecting member, and the second housing extension.

2. The motor according to claim 1, wherein
the rotor is disposed at an inner peripheral side in comparison with the stator, and
the hollow space is defined by an inner peripheral part of the rotor.

3. The motor according to claim 2, wherein
the unit to be detected is provided to be integrally rotatable with the rotor, and
a rotation of the detecting unit relative to the stator is regulated.

4. The motor according to claim 3, further comprising:
a light transmitting part that transmits radiated light and a light shielding part that shields the radiated light, the light transmitting part and the light shield part being alternately provided in a circumferential direction of the rotor in the unit to be detected; and
a radiating unit that radiates light to the unit to be detected and a light receiving unit that receives the light transmitted through the light transmitting unit, the radiating unit and the light receiving unit being provided in the detecting unit, wherein
the detecting unit detects the rotation state of the unit to be detected on the basis of a light reception result obtained by the light receiving unit.

5. The motor according to claim 1, further comprising:
an insertion member that includes:
a tubular inserting unit that is inserted into the inner peripheral sides of the rotor extension, the connecting member, the unit to be detected, the substrate, and the second housing extension, and
an insertion member extension that extends toward an outer peripheral side from the other end of the inserting unit and that is connected to the other end of the second housing, wherein
the through-hole is defined by an inner peripheral surface of the insertion member.

6. The motor according to claim 1, wherein
the stator has a three-phase winding, and
the encoder detects a phase of a current flowing in the three-phase winding.

* * * * *